United States Patent [19]

Hatsuda et al.

[11] Patent Number: 5,720,736
[45] Date of Patent: Feb. 24, 1998

[54] ABSORBENT MATERIAL, ABSORBENT ARTICLE, AND METHOD FOR PRODUCTION THEREOF

[75] Inventors: Takumi Hatsuda; Kazumasa Konishi, both of Hyogo, Japan

[73] Assignee: Nippon Shokubai Co., Ltd., Osaka, Japan

[21] Appl. No.: 611,559

[22] Filed: Mar. 6, 1996

Related U.S. Application Data

[62] Division of Ser. No. 465,614, Jun. 5, 1995, Pat. No. 5,518,761, which is a continuation of Ser. No. 112,900, Aug. 27, 1993, abandoned.

[30] Foreign Application Priority Data

Aug. 28, 1992 [JP] Japan .................................. 4-230443
Jan. 8, 1993 [JP] Japan .................................. 5-001550
Mar. 3, 1993 [JP] Japan .................................. 5-042939
Mar. 24, 1993 [JP] Japan .................................. 5-065104

[51] Int. Cl.$^6$ ........................................ A61F 13/15
[52] U.S. Cl. ...................... 604/368; 604/372; 427/180; 427/189; 442/417; 442/294
[58] Field of Search ........................ 604/358, 368, 604/372; 427/180, 189, 195; 428/286; 442/267, 294, 394, 398, 417

[56] References Cited

U.S. PATENT DOCUMENTS

| | | |
|---|---|---|
| 3,959,569 | 5/1976 | Burkholder, Jr. . |
| 4,055,180 | 10/1977 | Karami .................................. 604/368 |
| 4,699,619 | 10/1987 | Bernardin . |
| 4,798,603 | 1/1989 | Meyer et al. . |
| 4,826,880 | 5/1989 | Lesniak et al. . |
| 4,834,735 | 5/1989 | Alemany et al. . |
| 5,035,805 | 7/1991 | Freeman et al. . |
| 5,368,918 | 11/1994 | Harada et al. .................. 604/368 |
| 5,516,569 | 5/1996 | Veith et al. .................. 604/368 |
| 5,599,336 | 2/1997 | Plischke .................. 604/368 |

FOREIGN PATENT DOCUMENTS

| | | |
|---|---|---|
| 0 122 042 | 10/1984 | European Pat. Off. . |
| 0 443 627 | 8/1991 | European Pat. Off. . |
| 59-129232 | 7/1984 | Japan . |
| 60-232936 | 11/1985 | Japan . |
| 1-29881 | 6/1989 | Japan . |
| 2060018 | 4/1981 | United Kingdom .......... 604/368 |
| 2251206 | 1/1992 | United Kingdom . |
| WO 91/15362 | 10/1991 | WIPO . |

*Primary Examiner*—Robert A. Clarke
*Attorney, Agent, or Firm*—Burns, Doane, Swecker & Mathis, LLP

[57] ABSTRACT

An absorbent material is provided which enjoys suppleness, possesses highly satisfactory absorption qualities (speed of absorption and capacity for absorption), allows section into pieces of desired size and shape, and excels in safety.

An absorbent material comprising 100 parts by weight of absorbent resin particles and 15 to 150 parts by weight of water, which absorbent material is in the form of a sheet having a thickness in the approximate range of 0.3 to 5 mm, the form of a sheet resulting from mutual adhesion of the absorbent resin particles.

28 Claims, 3 Drawing Sheets

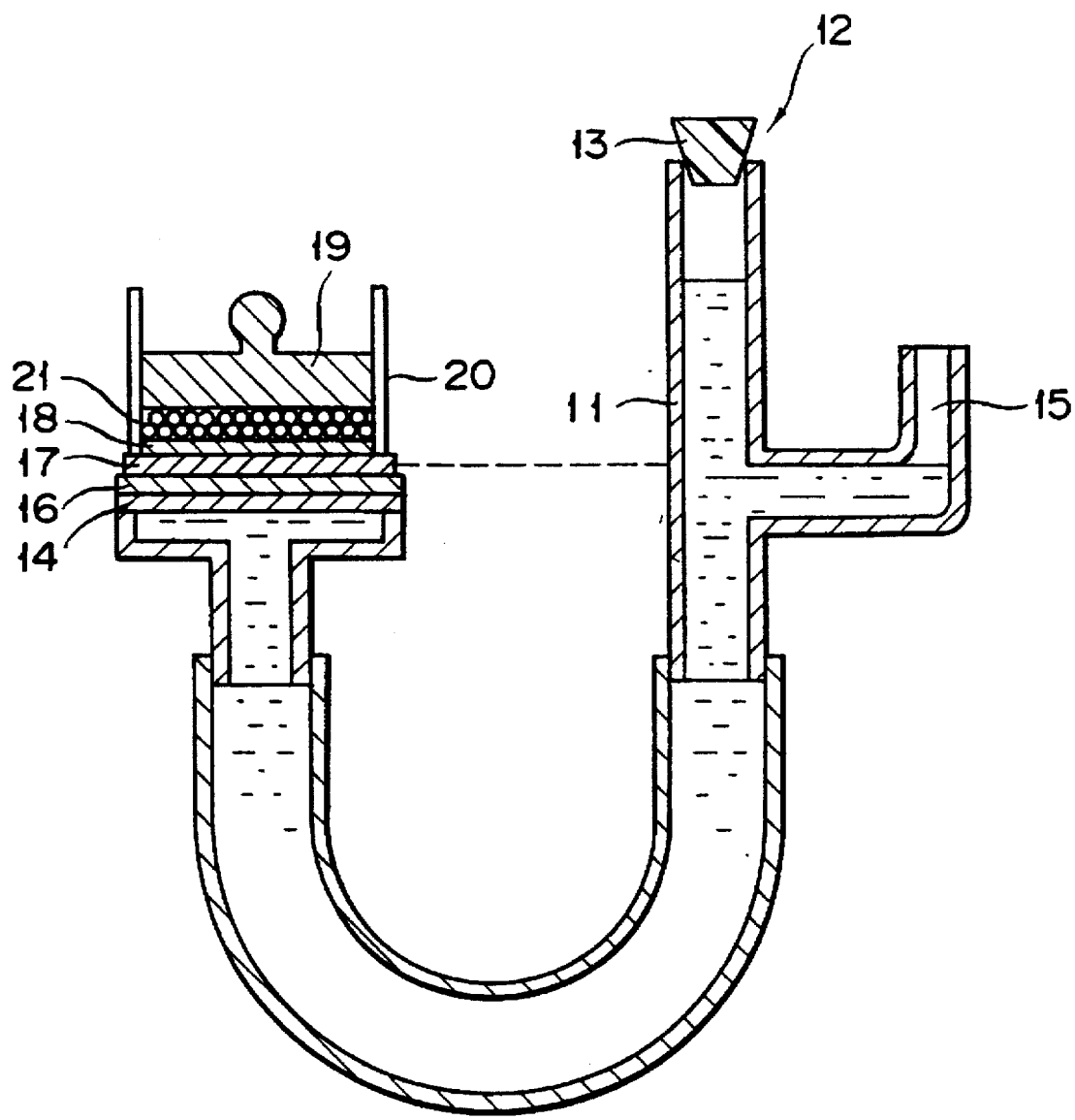

ABSORBENT MATERIAL, ABSORBENT ARTICLE, AND METHOD FOR PRODUCTION THEREOF

This application is a divisional of application Ser. No. 08/465,614, filed Jun. 5, 1995, now U.S. Pat. No. 5,518,761, which is a continuation of application Ser. No. 08/112,900, filed Aug. 27, 1993 (now abandoned).

TECHNICAL FIELD

This invention relates to a novel absorbent material and an absorbent article and a method for the production thereof. More particularly, it relates to a flexible sheetlike absorbent material possessing supple feeling and an ideal ability to absorb water and a flexible sheetlike absorbent material exhibiting a high speed of absorption and possessing outstanding flexibility, specifically an absorbent material composed of absorbent resin particles and water and consequently allowed to be cut in a desired size or shape and an absorbent article incorporating therein the absorbent material mentioned above.

BACKGROUND ART

As absorbent resins, cross-linked partially neutralized polyacrylic acid, saponified acrylic ester-vinyl acetate copolymers, modified cross-linked polyvinyl alcohols, cross-linked isobutylene-maleic anhydride copolymer, hydrolyzed starch-acrylonitrile graft polymer, starch-acrylic acid graft polymer, and partially cross-linked polyethylene oxide have been known to the art. These absorbent resins are widely used as sanitary napkins, disposable diapers, and other similar sanitary absorbent agents and as water-retaining agents and dehydrators in the field of agriculture and horticulture and the field of civil engineering, for example.

The absorbent resins are generally used in the form of fine powder or minute particles. In many cases of actual use, such an absorbent resin is converted preparatorily into a composite in the form of a sheet or a film as by being sandwiched with opposed sheets of paper, incorporated in pulp and compressed together by the use of the embossing technique, or melt sealed as with a thermoplastic resin.

Various proposals have been heretofore made for the purpose of realizing the use of the absorbent resin in the form of a sheet by a general procedure of depositing the absorbent resin on a substrate and subjecting the resultant composite to a treatment of fixation. They can be broadly divided into methods which comprise a first step of producing an absorbent resin and a subsequent step of molding the absorbent resin in the form of a sheet and methods which comprise a single step of effecting simultaneously the production of an absorbent resin and the molding of this resin in the form of a sheet. The former methods consist of (a) methods which comprise depositing an absorbent resin powder on a sheetlike substrate and subjecting the resultant composite to a treatment of fixation and (b) methods which comprise molding absorbent resin fibers in the form of a sheet. The methods of (b) are not very popular because the production of absorbent resin fibers itself is unduly expensive and the produced absorbent sheet is deficient in the ability to absorb water.

The methods (a) which are varied by the kind of treatment of fixation embrace a method which comprises spraying an absorbent resin powder on a substrate sheet, superposing another sheet thereon, and subjecting the resultant laminate to an embossing work, a method which comprises mixing an absorbent resin powder with a substrate sheet and subjecting the resultant mixture to an embossing work, methods which comprise imparting a small moisture content to an absorbent resin powder and ensuring powerful fixation of the absorbent resin power to a substrate sheet (such as are disclosed in U.S. Pat. No. 3,959,569, JP-A-51-40,497, JP-A-54-123, 293, JP-A-54-141,099, and JP-A-58-36,452), and methods which comprise realizing fixation of an absorbent resin powder to a substrate sheet by the use of a resinous binder (such as are disclosed in JP-A-58-101,047, JP-A-4-504,234, and U.S. Pat. No. 5,128,082), for example. JP-A-1-230,671 proposes a method for immobilizing an absorbent resin by combining the absorbent resin with an aqueous liquid thereby forming a hydrate. These methods, however, are at a disadvantage in entailing certain difficulties in the production of an absorbent sheet. For example, they essentially require to use a substrate for the purpose of retaining the absorbent resin powder in the form of a sheet, entail a complicate process for the formation of a composite of an absorbent resin powder with a substrate, jeopardize the work environment because an absorbent resin powder is liable to drift, and produce a sheet deficient in strength or flexibility. Further, since they are not allowed to increase the amount of an absorbent resin powder to be deposited per unit area of the substrate, they suffer from a small capacity for absorption and a small speed of absorption. If the amount of the absorbent resin to be deposited per unit area of the substrate is increased, the produced sheet gains in rigidity and tends to shed the deposited absorbent resin powder.

Several methods which comprise directly polymerizing a monomer on a substrate sheet thereby effecting simultaneously the production of an absorbent resin and the formation of a sheet have been proposed (such as are disclosed in JP-A-60-149,609, JP-A-62-53,309, JP-A-62-62,829, and JP-A-62-97,979), for example. These methods invariably suffer from the following drawbacks. The possibility that the polymerization initiator and other additives and a relatively large portion of the monomer used for the polymerization will survive the polymerization is high. Where these residual substances promise dubious safety, they pose a problem when the product of the polymerization is to be used as in sanitary articles or foodstuffs. Further, the reactions involved are difficult to control and deficient in productivity.

Absorbent articles which are intended to be incorporated in such sanitary goods as diapers, pads to be worn by adult incontinent patients, and sanitary articles have been known to the art (such as are disclosed in U.S. Pat. No. 4,699,619, U.S. Pat. No. 4,798,603, and U.S. Pat. No. 4,834,735). Generally, these absorbent articles are formed of a fibrous matrix and further of an absorbent resin as an optional component. The fibrous matrix is formed of either cellulose fibers known as wood pulp fluff or the combination of cellulose fibers with synthetic fibers.

Of the conventional absorbent articles, those which use no absorbent resin necessarily assume a large volume and prove to be unusually inconvenient to handle. Specifically, in these absorbent articles, the amount of water to be absorbed by the wood pulp fluff per unit weight of absorbent article is rather small (about 7 to 9 g/g), indicating that the wood pulp fluff must be used in a relatively large amount for the purpose of increasing the amount of water so absorbed to a desired level and, as a result, the produced absorbent article is relatively large and thick. In contrast to the wood pulp fluff, the absorbent resin has a considerably larger capacity for absorbing water (at least 15 g/g). Thus, the incorporation of an absorbent resin in an absorbent article permits a decrease in the amount of wood pulp fluff to be used. The use of an absorbent resin, therefore, allows production of a small and thin absorbent article. The conventional absorbent articles, however, still have a relatively small absorbent resin content (generally not more than about 50% by weight) and fall short of deserving to be designated as an ample small and thin absorbent article. When the amount of water to be absorbed per unit weight is taken into account, it is logically concluded that the increase in the amount of an absorbent resin ought to allow production of a compact and thin absorbent article. EP-A-443,627 proposes an absorbent article which has an increased absorbent resin content.

When an absorbent article is produced with a well-known absorbent resin incorporated therein at an increased content, various problems may arise. One of the problems consists in the phenomenon of gel blocking. Generally, when an absorbent resin absorbs water and swells, it deforms and fills up the empty spaces which formerly existed between adjacent absorbent resin particles and between the absorbent resin particles and a fibrous matrix and, as a result, obstructs the flow of a fluid formerly existed in the empty spaces. When the amount of an absorbent resin is small, the fibrous matrix is capable of repressing the mutual approach of adjacent absorbent resin particles and retaining a capillary structure enough for flow of the fluid in the matrix. Another problem resides in the insufficiency of the speed at which the absorbent resin absorbs. Generally, the speed of absorption by an absorbent resin is too small as compared with that by wood pulp fluff to cope favorably with the speed of fluid which is adopted in an absorbent article in the course of actual use of the absorbent article. Thus, the fibrous matrix such as of wood pulp fluff is used to function as a temporary storage layer for the fluid being handled by an absorbent article. Such is the true state of affairs.

EP-A-443,627 proposes an absorbent article which has an increased absorbent resin content owing to the use of an absorbent resin adapted to absorb water at a heightened speed. When the fibrous matrix fulfilling the role of fixing a particulate absorbent resin as proposed in EP-A-443,627 is present only in a small amount or totally absent, the problem of migration or maldistribution of an absorbent resin within an absorbent article is predictable. Generally, the absorbent resin is in the form of fine powder or of minute particles. Before or during the use of the absorbent article, therefore, the absorbent resin readily migrates within the absorbent article and induces the phenomenon of maldistribution unexpectedly and imparts a stable quality to the absorbent article only with difficulty. In the circumstances, the desirability of developing a method which is capable of disposing (fixing) an absorbent resin at a desired position in an absorbent article in spite of the problematic increase in the amount of the absorbent resin has found growing recognition. Heretofore, the practice of effecting the fixation of a particulate absorbent resin as by sandwiching the absorbent resin between opposed sheets of paper or by mixing the absorbent resin with a fibrous matrix such as of pulp and subsequently molding the resultant mixture in the form of sheet by such a treatment of fixation as the embossing work as already mentioned has been in vogue. These methods, however, encounter difficulties in coping with the case involving the problematic increase in the amount of an absorbent resin.

An attempt to produce a compact and thin absorbent article by increasing the amount of an absorbent resin results in the fact that in the produced absorbent article, the fibrous matrix which has played the role of fixing the absorbent resin is present in a small amount or totally absent. In this case, it is difficult to fix the resin at a prescribed position until after the absorbent resin has fulfilled the role of absorbing water and swelling with the absorbed water. Even when this fixation has been attained somehow or other until immediately before the absorbent article is put to use, it possibly becomes difficult to prevent the migration of gel at the time that the absorbent resin is swelled and gelled by absorbing water.

In the method which effects the treatment of fixation after having imparted an absorbent resin to a substrate, the produced composite is deficient in strength and incapable of preventing gel migration. When the absorbent resin has been thoroughly fixed, the produced composite exhibits an insufficient capacity for absorption. In the case of methods involving distribution of an absorbent resin among a plurality of cells (such as are disclosed in U.S. Pat. No. 5,035,805 and GB 2,251,206), the cells must be given a decreased size for the purpose of repressing the possible migration of the resin in an absorbent article prior to the use of the absorbent article. This decrease of size results in a decrease in the capacity of the absorbent article for absorption. Moreover, the process of forming numerous cells does not always prove to be highly productive.

This invention, therefore, has an object of providing a sheetlike absorbent material supple, tough, pleasant of touch, and excellent in the ability to absorb water and a method for the production thereof.

Another object of this invention is to provide an absorbent material which abounds with suppleness, possesses an ideal ability to absorb water (speed of absorption and amount of water absorbed), succumbs to section into pieces of desired size and shape, and enjoys high safety. A further object of the present invention is to provide a method for the production of the absorbent material mentioned above, which method operates with simplicity, abounds with productivity, and allows easy control of the performance of product. Still another object of this invention is to provide a compact and thin article using the absorbent material mentioned above.

Yet another object of this invention is to provide a sheetlike absorbent material which abounds with suppleness, exhibits an ideal ability to absorb water, and possesses physical properties excellent in stability to endure the effect of aging in an atmosphere of low humidity and a method for the production thereof.

A further object of this invention is to provide a compact and thin absorbent article using the sheetlike absorbent material mentioned above.

Still another object of this invention is to provide a thin absorbent article which possesses a large capacity for absorption of water, permits effective prevention of gel migration within the absorbent article in the course of use, and precludes deformation.

DISCLOSURE OF INVENTION

The objects described above are accomplished by an absorbent material comprising 100 parts by weight of absorbent resin particles and 15 to 150 parts by weight of water, which absorbent material is characterized by the fact the absorbent material is in the form of a sheet having a thickness in the approximate range of about 0.3 to 5 mm, and said form of a sheet results from mutual adhesion of said absorbent resin particles.

These objects are accomplished by an absorbent material comprising 100 parts by weight of absorbent resin particles, 15 to 150 parts by weight of water, and 0.1 to 10 parts by weight of at least one absorption auxiliary selected from the group consisting of water-insoluble minute particles, surfactants, and fibers, which absorbent material is characterized by the fact that the absorbent material is in the form of a sheet having a thickness in the approximate range of about 0.3 to 5 mm in thickness and said form of a sheet results from mutual adhesion of the absorbent resin particles.

These objects are accomplished by an absorbent material comprising 100 parts by weight of absorbent resin particles, 0.1 to 10 parts by weight of at least one absorption auxiliary selected from the group consisting of water-insoluble minute particles, surfactants, and fibers, 3 to 30 parts by weight of water, and 5 to 50 parts by weight of a polyhydric alcohol, which absorbent material is characterized by the fact that said absorbent material is in the form of a sheet having a thickness in the approximate range of about 0.3 to 5 mm and the form of a sheet results from mutual adhesion of the absorbent resin particles.

These objects are also accomplished by a laminated absorbent material having a water-permeable sheet on at least one surface of the absorbent material mentioned above.

These objects are further accomplished by an absorbent article characterized by containing the absorbent material mentioned above in a bag having at least one surface side thereof formed of a water-pervious sheet.

These objects are accomplished by a method for the production of an absorbent material, characterized by spreading 100 parts by weight of absorbent resin particles in the form of a planar layer having a thickness regulated in the approximate range of about 0.3 to 5 mm on a substrate and bringing 15 to 150 parts by weight of water and/or steam into contact with said planar layer without disturbing the constitution said planar layer.

These objects are also accomplished by a method for the production of an absorbent material, characterized by spreading 100 parts by weight of absorbent resin particles and 0.1 to 10 parts by weight of at least one absorption auxiliary selected from the group consisting of water-insoluble minute particles, surfactants, and fibers in the form of a planar layer having a thickness regulated in the approximate range of about 0.3 to 5 mm on a substrate and bringing 15 to 150 parts by weight of water and/or steam into contact with said planar layer without disturbing the constitution of said planar layer.

These objects are further accomplished by a method for the production of an absorbent material, characterized by spreading 100 parts by weight of absorbent resin particles and 0.1 to 10 parts by weight of at least one absorption auxiliary selected from the group consisting of water-insoluble minute particles, surfactants, and fibers in the form of a planar layer having a thickness regulated in the approximate range of about 0.3 to 5 mm on a substrate and bringing 3 to 30 parts by weight of water and 5 to 50 parts by weight of a polyhydric alcohol into contact with said planar layer without disturbing the constitution of said planar layer.

These objects are accomplished by an absorbent article having an absorbent material contained in a bag having at least one surface side thereof formed of a water-pervious sheet, which absorbent article is characterized by the fact that said absorbent material is sheetlike material comprising at least 60% by weight of an absorbent resin and is furnished with 3 to 15 points fixtures per about 1,000 cm$^2$ of surface area of said sheetlike material.

BRIEF DESCRIPTION OF DRAWINGS

FIG. 4 is a cross section of a device to be used in this invention for measuring absorption capacity under load.

BEST MODE FOR CARRYING OUT THE INVENTION

Figure 1:
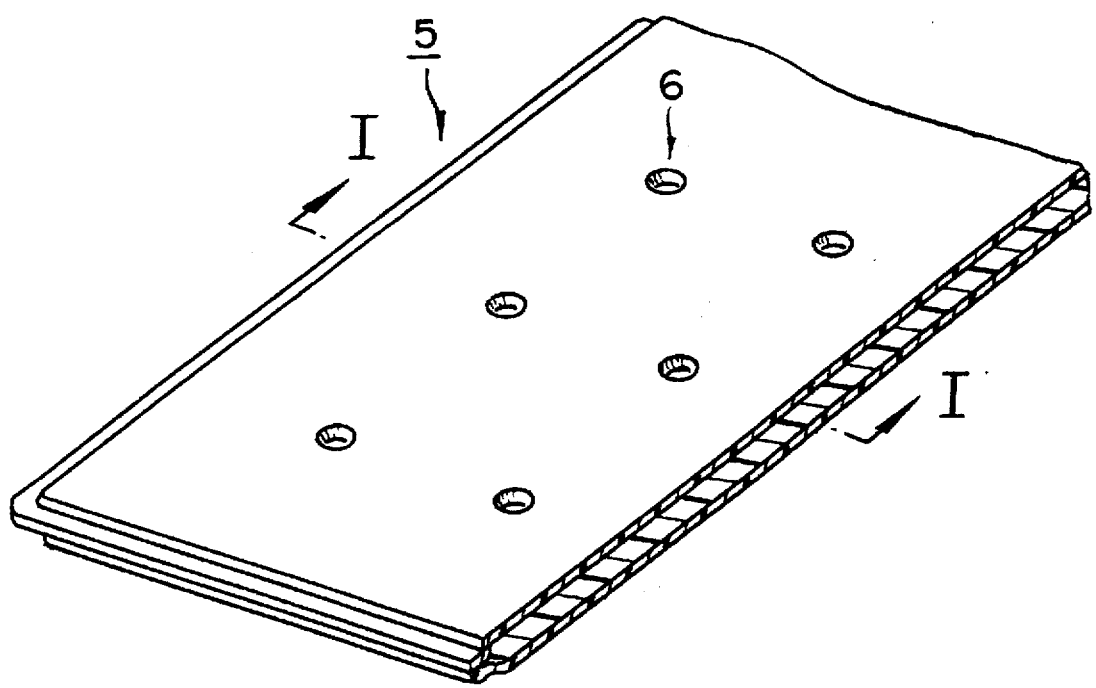
FIG. 1 is a perspective view illustrating one example of the absorbent article according with this invention.

Now, this invention will be described in detail below.

The absorbent resin particles to be used in this invention are particles of an absorbent resin. They have no particular restriction except for the requirement that they should be capable of absorbing water and expanding with the absorbed water. Generally they are obtained by polymerizing a water-soluble unsaturated monomer. As typical examples of the water-soluble unsaturated monomer, anionic monomers such as (meth)acrylic acids, maleic acid and maleic anhydride, fumaric acid, crotonic acid, itaconic acid, 2-(meth)acryloyl ethane sulfonic acids, 2-(meth)acryloyl propane sulfonic acids, 2-(meth)acrylamide-2-methyl propane sulfonic acids, vinyl sulfonic acid, and styrene sulfonic acid and salts thereof; nonionic hydrophilic group-containing monomers such as (meth)acryl amides, N-substituted (meth)acryl amides, 2-hydroxy propyl (meth) acrylates, methoxy polyethylene glycol (meth)acrylates, and polyethylene glycol (meth)acrylates; and amino group-containing unsaturated monomers such as N,N-dimethyl amino ethyl (meth)acrylates, N,N-dimethyl amino propyl (meth)acrylate, and N,N-dimethyl amino propyl (meth)acryl amides and the products of quaternization thereof may be cited. Such acrylic esters as, for example, methyl (meth) acrylates, ethyl (meth)acrylates, and butyl (meth)acrylates and such hydrophobic monomers as vinyl acetate and vinyl propionate may be used in an amount such as to avoid notably impeding the hydrophilicity of the produced polymer.

As the monomer component, one or more members 20 selected from the group of water-soluble monomers cited above may be used. In view of various absorption properties exhibited by the absorbent material to be finally produced, one member selected from the group consisting of (meth) acrylic acids (and salts), 2-(meth)acryloyl ethane sulfonic acids (and salts), 2-(meth)acryl amide-2-methyl propane sulfonic acids (and salts), (meth)acryl amides, methoxy polyethylene glycol (meth)acrylates, N,N-dimethyl amino ethyl (meth)acrylates, and the products of quaternization thereof proves to be a desirable choice. The monomer which contains as an essential component thereof one member selected from among (meth)acrylic acids (and salts) is more desirable. The (meth)acrylic acid which has a portion thereof in the range of 30 to 90 mol %, preferably 50 to 80 mol %, neutralized with a basic substance is used most desirably in this case. The absorbent resin is desired to have an absorption ratio in the approximate range of 20 to 60 g/g as determined by the method involving the immersion of a teabag containing a sample in a physiological saline solution. The proportion of the component surviving cross-linkage, i.e. the so-called water-insoluble component, is desired to be not more than 20% by weight, preferably not more than 10% by weight. It is desired to be still smaller.

The absorbent resin to be used in this invention may be of a self-cross-linking type obtainable without using any cross-linking agent or of a type obtainable by using a cross-linking agent containing a polymerizing unsaturated group and/or a reactive functional group to such an extent that the properties of the produced absorbent resin particles will reach desired levels.

As typical examples of the cross-linking agent answering the description given above, N,N'-methylene bis(meth)acryl amides, (poly)ethylene glycol di(meth)acrylates, glycerin tri(meth)-acrylates, trimethylol propane tri(meth)acrylates, triallyl amine, triallyl cyanurate, triallyl isocyanate, glycidyl (meth)-acrylates, (poly)ethylene glycols, diethylene glycol, (poly)-glycerins, propylene glycol, diethanol amine, trimethylol propane, pentaerythritol, (poly)ethylene glycol diglycidyl ethers, (poly)glycerol polyglycidyl ether, epichlorohydrin, ethylene diamine, polyethylene imine, (poly)aluminum chloride, aluminum sulfate, calcium chloride, and magnesium sulfate may be cited. One or more cross-linking agents to be selected from the group mentioned above in due consideration of reactivity may be used.

Further in the production of an absorbent resin, such a monomer component may be polymerized in the presence of a hydrophilic macromolecular substance like starch, cellulose, polyvinyl alcohol, or a similar so that a graft bond or complex will be formed simultaneously with the polymerization.

In the polymerization of the monomer component, such water-soluble radical polymerization initiators as ammonium persulfate, potassium persulfate, hydrogen peroxide, t-butyl hydroperoxide, and 2,2'-azo-bis-amidinopropane dihydrochloride are usable for the purpose of initiating the polymerization. The method of polymerization has no restriction of any sort. It may be any of the well-known methods such as, for example, bulk polymerization, aqueous solution polymerization, and reversed-phase suspension polymerization.

The absorbent resin is used in the form of a simple kind or a mixture of two or more kinds.

The absorbent resin particles which are used in the present invention are not particularly discriminated on account of the shape of particle. They may be in the form of flakes obtainable by drying in a drum or amorphous particles obtainable by grinding lumps of resin. Alternatively, they may be in the form of beads obtainable according to the method of reversed-phase suspension polymerization. Generally, the beads which are obtained by the reversed-phase suspension polymerization have a dispersant or a surfactant deposited on the surface thereof. In the case of the beads of this kind, it may occasionally prove desirable to have the beads additionally ground before they are put to use in this invention.

The absorbent resin particles to be used in this invention are only required to be in a particulate form enough to allow the accomplishment of the objects of this invention. They are not particularly discriminated on account of the size of particle. An attempt to impart exalted tensile yield strength and tensile yield elongation to the absorbent material of this invention generally shows an inclination toward allowing both the strength and elongation to increase in accordance as the size of particles decreases. For the purpose of allowing the produced absorbent material to acquire satisfactorily balanced magnitudes of tensile yield strength and tensile yield elongation, therefore, the absorbent resin particles are desired to have a particle size distribution such that they contain substantially no particle exceeding 1,000 µm in diameter and contain particles of 150 µm or less in diameter in a proportion of not less than 20%. Preferably this particle size distribution is such that substantially none of the particles has a diameter exceeding 850 µm and not less than 20% of the particles have diameters not exceeding 150 µm. For the purpose of allowing the produced absorbent material to acquire satisfactorily balanced magnitudes of absorption speed and flexibility, the absorbent resin particles are preferable to have a particle size distribution such that they contain substantially no particle exceeding 1,000 µmin diameter and contain particles of 150 µm or less in diameter in a proportion of not more than 10%. More preferably, this particle size distribution is such that substantially none of the particles has a diameter exceeding 850 µm and not less than 10% of the particles have diameters not exceeding 150 µm. Preferably, the absorbent resin particles have a particle size distribution such that substantially none of the particles has a diameter exceeding 600 µm and not more than 5% of the particles have diameters not exceeding 150 µm.

As an absorbent material excellent particularly in speed of absorption, this invention provides an absorbent material which contains at least one absorption auxiliary selected from the group comprising water-insoluble minute particles, surfactants, and fibers. The absorbent material is enabled to manifest a high speed of absorption by including therein the absorption auxiliary even if the absorbent resin particles used as the starting material happen to have a relatively wide particle size distribution. When the absorbent material contains an absorption auxiliary, the absorbent resin particles are rather desired to contain particles not exceeding 150 µm for the sake of the strength and absorption speed of the produced absorbent material. The absorbent resin particles, therefore, are desired to have a particle size distribution such that substantially none of the particles has a diameter exceeding 1,000 µm and not less than 10% of the particles have diameters not exceeding 150 µm. The possibility of rendering it difficult to produce the absorbent material in the form of a sheet arises when the absorbent resin particles contain particles not exceeding 150 µm in diameter in a low concentration. The speed of absorption tends to increase in accordance as the average particle diameter of the absorbent resin particles decreases.

In this invention, the absorbent material destined to have a high speed of absorption prefers use of such absorbent resin particles as exhibit a large absorption capacity under load. To be specific, the absorbent resin particles are desired to be capable of absorbing at least 20 ml of an aqueous 0.9 wt % sodium chloride solution per gram under a load of at least 20 g/cm$^2$ as determined by the method which will be specifically described hereinafter. The absorption capacity is more desirably at least 24 ml/g and still more desirably at least 28 ml/g. The absorbent material which has used absorbent resin particles having a larger absorption capacity under load than the specified lower limit is particularly excellent in speed of absorption. The absorbent resin particles which have such a large absorption capacity as mentioned above is obtained by subjecting the surface of the absorbent resin particles to a cross-linking treatment as described hereinafter.

There are times when the absorbent resin particles for use in this invention are desired to have a cross-linked surface. The absorbent material can be produced with a particularly excellent speed of absorption by using absorbent resin particles which have been prepared by mixing absorbent resin particles with a cross-linking agent possessing a group capable of reacting with at least two functional groups possessed by the resin particles and allowing the resin particles to react with the cross-linking agent and, as a result, have acquired an exalted cross-link density in the surface region of resin particle. Absorbent resin particles having a cross-linked surface can be obtained by subjecting absorbent resin particles to such a surface cross-linking treatment as is taught by methods which use a polyhydric alcohol (JP-A-58-180,233 and JP-A-61-16,903), a method which uses a polyglycidyl compound, a polyaziridine compound, a polyamine compound, or a polyisocyanate compound (JP-A-59-189,103), a method which uses glyoxal (JP-A-52-117, 393), methods which use a polyvalent metal (JP-A-51-136, 588 and JP-A-61-257,235, and JP-A-62-7,745), methods which use a silane coupling agent (JP-A-61-211,305, JP-A-61-252,212, JP-A-61-264,006), a method which uses an epoxy compound and a hydroxy compound (JP-A-2-132, 103), and a method which uses an alkylene carbonate (DE-A-402,780) respectively as a cross-linking agent. Besides, methods which necessitate the presence of an inert inorganic powder and JP-A-60-255,814), a method which requires the presence of a dihydric alcohol (JP-A-1-292, 004), and a method which calls for the presence of water and an ether compound (JP-A-2-153,903), for example, have been known to the art.

This invention does not discriminate the absorbent resin particles to be used therefor on account of the water content of resin particles so long as the absorbent resin can be effectively handled in the form of particles. The absorbent material which is obtained by adding 15 to 150 parts by weight of water and/or steam to 100 parts by weight of absorbent resin particles and establishing contact therebetween is only required to comprise 100 parts by weight of a substantially dry absorbent resin and 15 to 150 parts by weight of water. From the standpoint of workability, the absorbent resin particles to be used are desired to have a water content in the range of 0 to 40%, preferably 0 to 30%.

The absorbent material of this invention is composed of 100 parts by weight of absorbent resin particles and 15 to 150 parts by weight of water and caused to assume the form of a sheet owing to mutual adhesion of the absorbent resin particles. If the amount of the water contained in the absorbent material exceeds 150 parts by weight, the absorbent material betrays an inferior state of absorbent resin content, suffers from an unduly low capacity for absorption, and exhibits unduly low strength. If this amount of the water is less than 15 parts by weight, the produced absorbent material fails to exhibit sufficient strength or acquire the speed of absorption and the flexibility which are aimed at by this invention. The amount of the water more desirably is in the range of 25 to 100 parts by weight, and preferably in the range of 30 to 80 parts by weight, based on 100 parts by weight of absorbent resin particles. It is a surprising fact that given absorbent resin particles exhibit a much higher speed of absorption when they are used in a sheetlike absorbent material according with this invention than when they are used in the original particulate form.

The term "form of a sheet" as used in this invention refers to the fact that at least part of a pertinent absorbent material possesses a continuous plane. This sheet, for example, may contain one or more through holes of any desired shape. The sheet may otherwise be in an undulating form or a pleated form when desired. One of the opposite surfaces (obverse or reverse surface) of the absorbent material has an area of not less than 5 cm$^2$, desirably not less than 10 cm$^2$, and more desirably not less than 15 cm$^2$.

Further, the absorbent material of this invention is a material assuming the form of a sheet owing to mutual adhesion of absorbent resin particles. To be specific, the form of a continuous sheet is produced not because the absorbent resin particles are joined through the medium of such a third substance as an adhesive agent or a fibrous basal agent but because the absorbent resin particles are caused to adhere directly to one another. The expression "mutual adhesion of absorbent resin particles" as used herein refers to the fact that the adhesion occurs on a plurality of contiguously held absorbent resin particles when these resin particles are moistened. This adhesion has not entailed the formation of any such a chemical bond as a covalent bond between the adjacent absorbent resin particles. The explanation of the adhesion offered above can be inferred from the observation that the absorbent material of this invention is reverted to the absorbent resin particles after it has absorbed water and swelled with the absorbed water.

The absorbent material of this invention is in the form of a sheet 0.3 to 5 mm in thickness. If the thickness is less than 0.3 mm, the sheet is deficient in strength and in ease of handling. Further, the amount of absorbent resin per unit surface area is unduly small and the speed of swelling or the speed of absorption is likewise small. Conversely, if the thickness exceeds 5 mm, the absorbent sheet is not obtained easily with homogeneity and the speed of swelling or the speed of absorption tends to decrease. More desirably, the absorbent material is in the form of a sheet 0.5 to 3 mm in thickness. As previously stated, the technique of spraying absorbent resin particles on a sheet of substrate, superposing another sheet thereon, and converting the resultant laminate optionally with the aid of added water into a sheet has been known to the art. This conventional technique, however, is elaborately adapted to avoid mutual access of absorbent resin particles to the fullest possible extent and, as a result, the amount of absorbent resin particles to be effectively sprayed is 100 g/m$^2$ at most. The mutual adhesion of absorbent resin particles contemplated by this invention hardly occurs when the amount of sprayed absorbent resin particles is so small as mentioned above. The form of a sheet due to the mutual adhesion of absorbent resin particles, therefore, cannot be realized. The sheet of this invention is categorized by the expression that it should be handleable as one integral piece and is enabled to retain the designated form of a sheet owing to the mutual adhesion of absorbent resin particles.

The absorbent material of this invention is in the form of a sheet which results from mutual adhesion of absorbent resin particles. This sheet, on having absorbed a liquid subjected to absorption namely having directly contacted an aqueous medium, is disintegrated substantially into individual absorbent resin particles. This fact is believed to form a cause for the birth of an ideal ability to absorb water. The flexible absorbent sheets heretofore known to the art include a hydrogel polymer in the form of a thin film (JP-A-4-236, 203) and a film formed of polyvinyl alcohol and polyacrylic acid (or salt) (JP-B-62-921 and JP-B-2-48,024), for example. They invariably assume the form of an integral gel after absorbing a liquid and they are at a disadvantage in being unduly deficient in absorption ratio or in speed of absorption.

One preferred embodiment of this invention resides in an absorbent material which has a tensile yield strength of not less than 0.5 kg/cm$^2$ and a tensile yield elongation of not less than 10%. When an absorbent resin is to be handled in a large amount, insufficiency of the tensile yield strength possibly renders the handling of the absorbent resin difficult. Further in the handling of an absorbent material, insufficiency of the tensile yield elongation possibly renders the handling of the absorbent material difficult because of deficiency in flexibility. For the purpose of obtaining an absorbent material which answers the description given above, it is desirable to use absorbent resin particles having a particle size distribution such that substantially none of the particles has a diameter of not less than 1,000 μm and not less than 20% of the particles have diameters of not more than 150 μm. Preferably, the particle size distribution is such that substantially none of the particles has a diameter of not less than 850 μm and not less than 20% of the particles have diameters of not more than 150 μm. Generally, an exaltation of the strength or suppleness of the absorbent material as a sheet tends to decrease the speed of swelling or the speed of absorption.

Another preferred embodiment of this invention comprises an absorbent material which has a speed of absorption of not more than 50 seconds, preferably not more than 30 seconds, and a flexibility of not less than 90 degrees. The method for determining the speed of absorption will be specifically described hereinafter. The term "speed of absorption" as used in this invention is defined as the time which a sample absorbent material having a prescribed area spends in completely absorbing a fixed amount of artificial urine. It has been ascertained that an increase in the speed of absorption constitutes itself an essential requirement for the purpose of decreasing the amount of wood pulp fluff to be consumed and ensuring production of a small and thin absorbent article. The method for determining the flexibility of a sheet will be described hereinafter. The suppleness of an absorbent material, i.e. the index indicating the difficulty with which the sheet sheds fine dust on exposure to an external force, constitutes itself the flexibility used in this invention. If the flexibility is not sufficient, the sheet gains in stiffness of touch, fails to endure the impact of use, yields to disintegration, and sheds fine dust of absorbent resin particles. None of the heretofore known sheetlike absorbent materials resulting from mutual adhesion of absorbent resin particles simultaneously satisfies these physical properties. For the purpose of obtaining an absorbent material which answers the description given above, it is desirable to use absorbent resin particles having a particle size distribution such that substantially none of the particles has a diameter of not less than 1,000 μm and not more than 10% of the particles have diameters of not more than 150 μm. Desirably, the particle size distribution is such that substantially none of the particles has a diameter of not less than 850 μm and not more than 10% of the particles have diameters of not more than 150 μm. Still more desirably, the particle size distribution is such that substantially none of the particles has a diameter of not less than 600 μm and not more than 5% of the particles have diameters of not more than 150 μm. Further, the absorbent resin particles are desired to have an absorption ratio under load of at least 20 ml/g as mentioned above and they are desired to have undergone a surface cross-linking treatment.

This invention provides an absorbent material comprising 100 parts by weight of absorbent resin particles, 15 to 150 parts by weight of water, and 0.1 to 10 parts by weight of at least one absorption auxiliary selected from the group consisting of water-insoluble minute particles, surfactants, and fibers, which absorbent material is characterized by the fact that the absorbent material is in the form of a sheet about 0.3 to 5 mm in thickness and the form of a sheet has resulted from mutual adhesion of the absorbent resin particles. When the absorbent material is made to contain a specific absorption auxiliary, it acquires an ideal speed of absorption.

The term "absorption auxiliary" as used herein refers to what functions to enable the absorbent material of this invention in the process of absorption to exhibit an exalted speed of absorption. The absorption auxiliary comprises at least one member selected from the group consisting of water-insoluble minute particles (both inorganic minute particles and organic minute particles), surfactants, and fibers. The following are typical examples of the absorption auxiliary. As examples of surfactants, polyoxyethylene alkyl ethers, Polyoxyethylene alkyl phenol ethers, sorbitan fatty acid esters, Polyoxyethylene sorbitan fatty acid esters, Polyoxyethylene acyl esters, oxyethyleneoxypropylene block copolymers, and sucrose fatty acid esters may be cited. As examples of inorganic minute particles, mica, pyrophanite, kaolinite, hulsite, other similar clayish minerals, and finely divided silica preparations made chiefly of silicon dioxide particles having an average particle diameter of not more than 50 μm (produced by Japan Aerosil Ltd. and marketed under trademark designation of "Aerosil 200") and (produced by Shionogi & Co., Ltd. and marketed under trademark designation of "Carplex #80) may be cited.

As examples of organic minute particles, carbon black, activated carbon, and powdered pulp may be cited. Among other minute particles, finely divided silica proves to be desirable because of the ability thereof to exalt the speed of absorption. The amount of the absorption auxiliary to be effectively used herein is in the range of 0.1 to 10 parts by weight, more desirably 0.5 to 5 parts by weight, and most desirably 0.7 to 2 parts by weight. If the amount of the absorption auxiliary exceeds 10 parts by weight, the excess fails to bring about a proportional addition to the effect and rather lowers the capacity for absorption and at times renders the formation of a sheet difficult. If the amount is less than 0.1 part by weight, the effect of the use of this absorption auxiliary is not obtained.

For the production of an absorbent material which, as a particularly preferred embodiment of this invention, possesses a speed of absorption of not more than 30 seconds and a flexibility of not more than 90 degrees, it is ideal to use absorbent resin particles having a particle side distribution such that substantially none of the particles have a diameter of not less than 1,000 μm and not less than 10% of the particles have diameters of not more than 150 μm and further use an absorption auxiliary. A deficient content of the particles which have diameters of not more than 150 μm possibly results in rendering it difficult to produce an absorbent material in the form of a sheet. It is desirable for the sake of obtaining an absorbent material with a high speed of absorption to use an absorption auxiliary and absorbent resin particles which have such a specific particle size distribution and such a specific absorption ratio under load as mentioned above. Further, the absorbent resin particles are desired to have undergone a surface cross-linking treatment.

This invention further provides a method for obtaining such an absorbent material as described above with highly satisfactory productivity. This method of production comprises spreading 100 parts by weight of absorbent resin particles in the form of a planar layer having a thickness regulated in the approximate range of about 0.3 to 5 mm on a substrate and bringing 15 to 150 parts by weight of water and/or steam into contact with said planar layer without disturbing the constitution of said planar layer.

Another method of production according with this invention comprises spreading 100 parts by weight of absorbent resin particles and 0.1 to 10 parts by weight of at least one absorption auxiliary selected from the group consisting of water-insoluble minute particles, surfactants, and fibers together in the form of a planar layer having a thickness regulated in the approximate range of about 0.3 to 5 mm on a substrate and bringing 15 to 150 parts by weight of water and/or steam into contact with said planar layer without disturbing the constitution of said planar layer. The expression "bringing water and/or steam into contact with planar layer without disturbing the constitution of said planer layer" means adding water and/or steam to the absorbent resin particles in such a manner that this addition exerts substantially no shearing force on the absorbent resin particles. The addition of this nature is accomplished by a method of spraying water onto absorbent resin particles spread on a substrate in the form of a layer of a thickness regulated in the approximate thickness of about 0.3 to 5 mm, a method of likewise spraying saturated steam, and a method of retaining in an atmosphere of a relative humidity of not less than 50% absorbent resin particles spread in the form of a layer with a regulated thickness on a substrate, for example.

Lack of uniformity in the contact between the absorbent resin particles and water possibly results in failure of a produced sheet to enjoy homogeneity. A homogeneous sheet is obtained by causing the layer of absorbent resin particles which has contacted water to be sealed, for example, so as to preclude the otherwise possible vaporization of the water keeping now the resin particles wet and then allowing the sealed layer to stand at rest preferably at a temperature exceeding 30° C. When absorbent resin particles and water added thereto are stirred together, for example, the motion of this stirring may exert shearing force on the nascent mixture. The shearing force is undesirable because it degrades the speed of absorption of the produced absorbent material. In consequence of such an operation as described above, the absorbent resin particles in the blend tend to gather and form lumps. It is difficult to obtain a sheetlike absorbent material as aimed at by this invention from these lumps. Though these lumps are not incapable of being molded in the form of a sheet, the operation of this molding not only consumes an unusually large amount of energy but also suffers mutual adhesion of absorbent resin particles to proceed excessively. In an extreme case, the adhesion entails extinction of the boundaries between adjacent resin particles. The sheet which is obtained in consequence of the operation of stirring tends to suffer from serious loss of the speed of absorption. Even after the absorbent material of this invention has been produced, it is desirable to prevent the product from being exposed to the shearing force.

In the method of production according with this invention, absorbent resin particles are spread in the form of a planar layer having a thickness regulated in the approximate range of about 0.3 to 5 mm on a substrate in preparation for contact of the absorbent resin particles with water and/or steam. If the thickness of the planar layer is less than 0.3 mm, the sheet to be consequently obtained betrays deficiency in strength and ease of handling and suffers from an undue decrease in the amount of absorbent resins per unit area and the produced absorbent material manifests an unduly low speed of absorption. Further, the sheet encounters difficulties in retaining the initial shape thereof as a sheet. For the purpose of accomplishing the thickness defined above, the absorbent resin particles are generally required to be used in a ratio of not less than 200 g/m$^2$, preferably not less than 250 g/m$^2$, and more preferably not less than 300 g/m$^2$. Conversely, if the thickness exceeds 5 mm, the speed of absorption exhibited by the produced absorbent material tends to decrease and the time to be spent in establishing contact between the absorbent resin particles and water and/or steam for the purpose of obtaining a homogeneous absorbent material tends to elongate conspicuously. In the method of production according with this invention, the amount of water to be added to absorbent resin particles is in the range of 15 to 150 parts by weight based on 100 parts by weight of the absorbent resin particles.

The absorbent resin particles in question by nature are allowed to contain a certain amount of water as described above and are only required to be such in quality that they will be handled in a particulate form. When the absorbent resin particles inherently contain water, the amount of water to be added to the absorbent resin particles is such that the produced absorbent material has a water content in the range of 15 to 150 parts by weight based on 100 parts by weight of the absorbent resin particles present in the absorbent material. Incidentally, the method of this invention requires addition of at least 15 parts by weight of water to 100 parts by weight of absorbent resin particles for the purpose of producing an absorbent material in the form of a sheet. Where an absorbent material containing water in a ratio of 15 parts by weight based on 100 parts by weight of absorbent resin particles is to be produced, therefore, it is necessary to use absorbent resin particles whose water content is 0. If the amount of water exceeds 150 parts by weight, the possibility ensues that not only the capacity of the produced absorbent material for absorption will be lowered but also the absorbent material of the form of a sheet will sustain breakage during the course of production. Conversely, if the amount of water is less than 15 parts by weight, the possibility arises that not only the produced absorbent material will fail to acquire the speed of absorption and the flexibility aimed at by the invention but also the absorbent material will suffer from deficiency in strength due to inferior mutual adhesion of the absorbent resin particles. The amount of water is more desirably in the range of 25 to 100 parts by weight and most desirably in the range of 30 to 80 parts by weight, both based on 100 parts by weight of absorbent resin particles.

When absorbent resin particles and an absorption auxiliary are to be combined, no particular restriction is imposed on the kind of procedure to be used for this combination. Either a method which comprises preparatorily mixing absorbent resin particles with an absorption auxiliary and then bringing water into contact with the resultant mixture or a method which comprises preparatorily dissolving or dispersing an absorption auxiliary and then bringing the resultant aqueous solution or suspension into contact with absorbent resin particles may be used.

When absorbent resin particles are spread on a substrate and exposed to water and/or steam in the process of production of an absorbent material by the method of this invention, the spreading may be effected by any means of free choice. For example, an absorbent material of the form of a unitary sheet with a uniform thickness is obtained by spreading absorbent resin particles in a uniform thickness on a substrate throughout the entire surface thereof and an absorbent material is produced in a desired thickness with a desired pattern by spreading absorbent resin particles in corresponding thickness and pattern.

In the production of an absorbent material by the method of this invention, the water for contact with the spread layer of absorbent resin particles may be distilled water, deionized water, tap water, or industrial grade purified water, whichever suits the occasion. The water selected for use herein may have an inorganic substance or an organic substance dissolved or dispersed therein.

This invention further provides a laminated absorbent material having a water-pervious sheet superposed on at least one surface of an absorbent material comprising 100 parts by weight of absorbent resin particles and 15 to 150 parts by weight of water, which absorbent material is characterized by the fact that said absorbent material is in the form of a sheet having a thickness in the approximate range of about 0.3 to 5 mm and said form of a sheet results from mutual adhesion of said absorbent resin particles and a laminated absorbent material having a water-pervious sheet superposed on at least one surface of an absorbent material comprising 100 parts by weight of absorbent resin particles, 15 to 150 parts by weight of water, and 0.1 to 10 parts by weight of at least one absorption auxiliary selected from the group consisting of water-insoluble minute particles, surfactants, and fibers, which absorbent material is characterized by the fact that said absorbent material is in the form of a sheet having a thickness in the approximate range of about 0.3 to 5 mm and said form of a sheet results from mutual adhesion of said absorbent resin particles.

The laminated absorbent material of this invention is allowed to have the water-permeable sheet deposited on at least one surface or on both surfaces of the absorbent material mentioned above. It may have a water-permeable sheet deposited on one surface and a water-impermeable sheet deposited on the other surface as occasion demands. Though this laminated absorbent material can be obtained by merely superposing the water-permeable sheet or water-impermeable sheet on the absorbent material mentioned above, it may be subjected to a treatment such as embossing or lamination, for example. Where the speed of absorption counts much, the operation of pressing or embossing is undesirable because it is fated to exert pressure or shearing force. The laminated absorbent material can be otherwise produced by forming the absorbent material mentioned above on the water-permeable sheet or the water-impermeable sheet.

The laminated absorbent material of this kind can be produced by various procedures such as are cited below.

(1) A procedure which comprises spraying water onto a water-impermeable sheet, then spreading absorbent resin particles on the wetted sheet, subsequently covering the layer of resin particles deposited on the sheet with a water-permeable sheet, and further spraying water onto the covered layer on the sheet when necessary.

(2) A procedure which comprises spreading absorbent resin particles on a water-impermeable sheet, spraying water onto the layer of resin particles deposited on the sheet, then covering the wetted layer on the sheet with a water-permeable sheet, and further spraying water onto the covered layer on the sheet when necessary.

(3) A procedure which comprises spraying water onto a water-permeable sheet, then spreading absorbent resin particles onto the wetted sheet, subsequently covering the layer of resin particles deposited on the sheet with a water-permeable sheet, and further spraying water onto the covered layer on the sheet when necessary.

(4) A procedure which comprises spreading absorbent resin particles on a water-permeable sheet, then spraying water onto the layer of resin particles on the sheet, subsequently covering the wetted layer on the sheet with a water-permeable sheet, and further spraying water onto the covered layer on the sheet when necessary.

As typical examples of the water-permeable sheet usable effectively herein, regenerated cellulose type non-woven fabrics; fibrous substrates formed of such wood pulp fibers as mechanical pulp derived from wood, chemical pulp, semichemical pulp, and dissolving pulp; hydrophilic fibrous substrates made of such synthetic cellulose fibers as rayon and acetate; and cotton card web and paper may be cited. The water-permeable sheet is desired to have a texture which allows ready permeation of water. As concrete examples of the water-impermeable sheet usable effectively herein, films of nylon, polyethylene, polypropylene, polystyrene, and polyvinyl chloride may be cited.

Besides, this invention provides an absorbent material comprising 100 parts by weight of absorbent resin particles, 0.1 to 10 parts by weight of at least one absorption auxiliary selected from the group consisting of water-insoluble minute particles, surfactants, and fibers, 3 to 30 parts by weight of water, and 5 to 50 parts by weight of a polyhydric alcohol, which absorbent material is in the form of a sheet having a thickness in the approximate range of about 0.3 to 5 mm, and this form of a sheet results from mutual adhesion of the absorbent resin particles.

The absorbent resin to be used for this invention are as described above.

The absorbent resin particles for use in this invention are not particularly restricted by size but instead are only required to be in such a particulate form that they will permit this invention to be effectively operated thereon. Generally, the produced absorbent material shows an inclination to increase the speed of absorption rather when the absorbent resin particles used therein have a relatively small size. In terms of the ease with which the resin particles are handled and the permeability which a gel formed between the resin particles and absorbed liquid exhibits to a liquid, unduly minute resin particles are undesirable. If the amount of resin particles having diameters exceeding 1,000 μm increases beyond the upper limit, the absorbent material suffers from a deficiency in the speed of absorption. The fact that absorbent resin particles have a particle size distribution such that substantially none of the particles has a diameter of not less than 1,000 μm and not less than 10% of the particles have diameters of not more than 150 μm, therefore, proves to be desirable for the purpose of enabling a produced absorbent material to exhibit speed of absorption and flexibility in ideally balanced magnitudes. More desirably, the absorbent resin particles have a particle size distribution such that substantially one of the particles has a diameter of not less than 850 μm and not less than 10% of the particles have diameters of not more than 150 μm. From the viewpoint of ease of handling and permeability to liquid, the particle size distribution is desired to be such that the particles having diameters of not more than 150 μm falls in the range of 10 to 60%, preferably in the range of 10 to 30%.

The water content of the absorbent resin particles to bemused for this invention has no particular restriction imposed thereon. When an absorbent material of this invention has been obtained by the addition of water, the water content thereof is only required to be such that the amount of water present therein is in the range of 3 to 30 parts by weight, preferably 5 to 20 parts by weight, based on 100 parts by weight of the absorbent resin particles in a substantially dry state. From the viewpoint of workability, it is desirable to use absorbent resin particles having a water content of not more than 10%, preferably not more than 5%.

The absorbent material of this invention comprises 100 parts by weight of absorbent resin particles, 0.1 to 10 parts by weight of an absorption auxiliary, 3 to 30 parts by weight of water, and 5 to 50 parts by weight of a polyhydric alcohol and besides assumes the form of a sheet resulting from mutual adhesion of the absorbent resin particles. If the water content exceeds 30 parts by weight, the produced absorbent material suffers the physical properties thereof such as, for example, the speed of absorption and the flexibility, to be degraded to the extent of ceasing to withstand the effect of aging in an atmosphere of low humidity. Conversely, if the water content is less than 3 parts by weight, it is no longer possible to obtain an absorbent material in the form of a sheet. If the amount of a polyhydric alcohol exceeds 50 parts by weight, the excess brings about no proportional addition to the effect thereof but rather contributes to lower the capacity of the produced material for absorption. If the amount of the polyhydric alcohol is conversely less than 5 parts by weight, it is no longer possible to obtain an absorbent material in the form of a sheet having high flexibility to withstand the effect of aging. More desirably, the amount of water is in the range of 5 to 20 parts by weight and, at the same time, that of a polyhydric alcohol in the range of 5 to 30 parts by weight. The amounts of a polyhydric alcohol and water to be desirably incorporated in a given absorbent material are such that the weight ratio of the polyhydric alcohol to water is not less than 1. If this weight ratio is less than 1, the possibility arises that the produced absorbent material will have the flexibility thereof degraded to the extent of ceasing to withstand the effect of aging. Surprisingly, when absorbent resin particles in a particulate form are combined with such amounts of a polyhydric alcohol and water as fall in the range mentioned above to produce an absorbent material in the form of a sheet according with this invention, the produced absorbent material acquires a conspicuously exalted speed of absorption and excels in the stability of the speed of absorption and that of the flexibility to withstand the effect of aging as compared with an absorbent material using the absorbent resin particles in the particulate form.

As typical examples of the polyhydric alcohol to be used effectively in this invention, ethylene glycol, diethylene glycol, triethylene glycol, tetraethylene glycol, polyethylene glycol, propylene glycol, trimethylene glycol, dipropylene glycol, 2,2,4-trimethyl-1,3-pentadiol, polypropylene glycol, glycerol, 2-butene-1,4-diol, 1,4-butanediol, 1,5-pentanediol, 1,6-hexanediol, 1,2-cyclohexane dimethanol, 1,2-cyclohexanol, trimethylol propane, diethanolamine, triethanolamine, polyoxy propylene, oxyethylene-oxypropylene block copolymer, penta-erythritol, and sorbitol may be cited. Glycerol, polyglycerol, ethylene glycol, diethylene glycol, triethylene glycol, and trimethylene glycol prove to be desirable among other polyhydric alcohols mentioned above. Glycerol, ethylene glycol, diethylene glycol, and polyglycerol are particularly desirable.

The absorption auxiliary to be used in this invention is as described above.

The term "in the form of a planar layer" as used in this invention refers to the possession of an at least partly continuous surface. For example, a sheet which has a plurality of through holes of a desired shape answer the description. The sheet may be in an undulating form or a pleated form. One surface (obverse surface or reverse surface) of this sheet is desired to have an area of not less than 5 cm$^2$, preferably not less than 10 cm$^2$, and more preferably not less than 15 cm$^2$. Further, the absorbent material of this invention is a material in the form of a sheet resulting from mutual adhesion of absorbent resin particles. To be specific, the absorbent material has not assumed the form of a continuous sheet through the medium of such a third substance as an adhesive agent or a fibrous substrate, for example, but has assumes the form of a continuous sheet owing to mutual adhesion of absorbent resin particles. The expression "mutual adhesion of absorbent resin particles" as used herein refers to the adhesion which occurs when a multiplicity of absorbent resin particles held contiguously to one another are moistened. This adhesion produces no such chemical bond as covalent bond between the original absorbent resin particles. This fact is evinced by the observation that an absorbent material according with this invention, on being swelled with absorbed liquid, is reverted into a discrete mass of absorbent resin particles.

The absorbent material of this invention is in the form of a sheet having a thickness in the range of 0.3 to 5 mm. If this thickness is less than 0.3 mm, the sheet is deficient not only in strength but also in ease of handling. Besides, the produced absorbent material has an unduly small absorbent resin content per unit area and shows deficiency in the speed of absorption. Conversely, if the thickness exceeds 5 mm, an absorbent sheet of homogeneous quality is no longer obtained easily and the speed of absorption tends to decrease. More desirably, the absorbent material is in the form of a sheet having a thickness in the range of 0.5 to 3 mm. The technique of spreading absorbent resin particles on a substrate sheet, superposing another sheet on the layer of resin particles deposited on the substrate sheet, and moistening the covered layer on the substrate sheet, when necessary, thereby giving rise to a sheet has been known to the art as described previously. Since this conventional technique is elaborately adapted to preclude mutual approach of absorbent resin particles, however, the amount of absorbent resin particles which are spread at all is 100 g/m$^2$ at most. With such a small ratio of spreading, the mutual adhesion of absorbent resin particles contemplated by this invention is hardly accomplished and, as a result, the sheet resulting from mutual adhesion of resin particles cannot be realized. The sheet of this invention is such that it can be handled as a unitary sheet and can retain the form of a sheet owing to mutual adhesion of absorbent resin particles.

The absorbent material according with this invention is an article in the form of a sheet resulting from mutual adhesion of absorbent resin particles and, on exposure to a liquid subjected to absorption, namely an aqueous medium, is substantially disintegrated into individual absorbent resin particles.

One preferred embodiment of this invention comprises an absorbent material which manifests a speed of absorption of not more than 50 seconds and a flexibility of not less than 90 degrees in spite of the effect of aging. The method for determining the speed of absorption under the condition of aging will be described specifically hereinafter. The expression "speed of absorption under the condition of aging" as used in this invention is defined as the time which a given absorbent material prepared in a prescribed surface area and retained in an atmosphere of low humidity spends in completely absorbing a stated amount of synthetic urine. It has been ascertained that a large speed of absorption under the condition of aging is necessary for the purpose of decreasing the amount of wood pulp fluff to be consumed and permitting production of a small and thin absorbent article retaining physical properties stably in spite of the effect of aging. More preferably, the speed of absorption under the condition of aging is not more than 30 seconds. The method for determining the flexibility under the condition of aging will be described specifically hereinafter. The index indicating the flexibility which a given absorbent material manifests after standing in an atmosphere of low humidity and the difficulty with which the absorbent resin particles shed find dust after exposure to an external force constitutes the degree of flexibility under the condition of agent contemplated by this invention. If the flexibility is insufficient, the absorbent material gains in stiff feeling, ceases to withstand the impact of actual use, succumbs to destruction of planar layer, and wears to the point that the absorbent resin particles are visible. None of the existing sheetlike materials obtained in consequence of mutual adhesion of absorbent resin particles is found to satisfy simultaneously these physical properties. For the purpose of obtaining an absorbent material satisfying these physical properties, it is desirable to use absorbent resin particles which have a particle size distribution such that substantially one of the particles has a diameter of not less than 1,000 µm and not less than 10% of the particles have diameter of not more than 150 µm. More desirably, this particle size distribution is such that substantially none of the particles has a diameter of not less than 850 µm and not less than 10% of the particles have diameters of not more than 150 µm. From the viewpoint of the ease of handling and the permeability to liquid, absorbent resin particles have a particle size distribution such that particles having diameters of not more than 150 µm account for a proportion in the range of 10 to 60%, preferably 10 to 30%, of all the particles. Further, the absorbent resin particles are desired to have an absorption ratio under load of at least 20 ml/g as described above and they are desired to have undergone a surface cross-linking treatment.

This invention further provides a method for manufacturing the absorbent material described above with highly satisfactory productivity. Specifically, this method of production comprises spreading 100 parts by weight of absorbent resin particles and 0.1 to 10 parts by weight of at least one absorption auxiliary selected from the group consisting of water-insoluble minute particles, surfactants, and fibers together in the form of a planar layer having a thickness regulated in the approximate range of about 0.3 to 5 mm on a substrate and adding 3 to 30 parts by weight of water and 5 to 50 parts by weight of a polyhydric alcohol to the planar layer of absorbent resin particles without disturbing the constitution of the planar layer for thereby establishing contact therebetween.

The expression "spreading absorbent resin particles and an absorption auxiliary in the form of a planar layer having a thickness regulated and bringing water and a polyhydric alcohol into contact with said planar layer without disturbing the constitution of said planar layer" means that water and the polyhydric alcohol are added to the absorbent resin particles and the absorption auxiliary in such a manner that substantially no shearing force will be exerted on the planar layer. This operation can be effected, for example, by a method which comprises spreading absorbent resin particles on a substrate in a thickness regulated in the approximate range of about 0.3 to 5 mm and spraying the aqueous solution of a polyhydric alcohol onto the layer of resin particles, a method which comprises spraying the polyhydric alcohol onto the layer of resin particles and then either applying saturated steam to the layer or allowing the layer to stand in an atmosphere of a relative humidity of not less than 50%, or a method which comprises spraying water onto the layer of resin particles and then spraying the polyhydric alcohol onto the layer. Among other methods cited above, the method which uses the aqueous solution of a polyhydric alcohol for moistening the layer of resin particles proves to be particularly desirable. During the addition of water and a polyhydric alcohol to absorbent resin particles and an absorption auxiliary, when the absorbent resin particles and the absorption auxiliary are subjected in conjunction with water or the polyhydric alcohol to such an action as stirring which exerts shearing force on the nascent mixture, the disadvantage ensues that the speed of absorption of the produced absorbent material will be degraded by the shearing force. If this action is carried out, the absorbent resin particles show an inclination to conglomerate. It is difficult to manufacture the result of this conglomeration into an absorbent material in the form of a sheet aimed at by this invention. It is not impossible to mold these lumps into a sheet. The operation involved in this molding, however, not only consumes an extremely large energy but also suffers mutual adhesion of absorbent resin particles to proceed to an excessive degree. In an extreme case, the mutual adhesion could result in extinction of the boundaries between the particles. The sheet to be obtained in this case tends to suffer conspicuous decline of the speed of absorption.

When absorbent resin particles are combined with an absorption auxiliary, the procedure to be followed for the combination has no particular restriction. The combination may be attained, for example, by a method which comprises mixing absorbent resin particles preparatorily with an absorption auxiliary and then bringing water and a polyhydric alcohol into contact with the resultant mixture or a method which comprises dissolving or dispersing an absorption auxiliary in water and bringing the resultant aqueous solution or dispersion together with a polyhydric alcohol into contact with absorbent resin particles. The former method is more preferable than the latter method.

In the method of production according with this invention, prior to the contact of water and a polyhydric alcohol with absorbent resin particles and an absorption auxiliary, the absorbent resin particles and the absorption auxiliary are spread in the form of a planar layer having a thickness regulated in the approximate range of about 0.3 to 5 mm on a substrate. If the thickness of the planar layer is less than 0.3 mm, the absorbent sheet consequently produced is deficient in strength and ease of handling, has an unduly small absorbent resin content per unit surface area, and suffers from an unduly low speed of absorption. Besides, the produced sheet retains the shape thereof only with difficulty. To accomplish this thickness, it is generally necessary that the sheet should contain absorbent resin particles at a ratio of not less than 200 g/m$^2$, preferably not less than 250 g/m$^2$, and more preferably not less than 300 g/m$^2$. Conversely, if the thickness exceeds 5 mm, the produced absorbent material tends to have the speed of absorption rather lowered than otherwise and the contact of absorbent resin particles and an absorption auxiliary with water and a polyhydric alcohol tends to become incomplete. The time which is required for the perfection of a sheetlike absorbent material, therefore, is elongated notably.

When absorbent resin particles and an absorption auxiliary are spread on a substrate and water and a polyhydric alcohol are brought into contact thereto in the method for the production of an absorbent material of this invention, the manner in which the spreading is effected is a matter for free choice. A unitary sheetlike absorbent material is obtained with a uniform thickness by causing absorbent resin particles and an absorption auxiliary to be spread on a substrate in a uniform thickness throughout the entire surface of the substrate. When they are spread in a desired pattern with a desired thickness on a substrate, an absorbent material is obtained with corresponding thickness and pattern.

In the method of production according with this invention, the amount of water to be added to absorbent resin particles is in the range of 3 to 30 parts by weight based on 100 parts by weight of the absorbent resin particles. The absorbent resin particles in this case may contain water from the beginning in such an amount that the resin particles will be satisfactorily handled as a particulate substance. If this amount of water exceeds 30 parts by weight, the produced absorbent material has an unduly low absorbent resin content and consequently an unduly small capacity for absorption and, at the same time, the speed of absorption and the flexibility of the absorbent material have poor stability to withstand the effect of aging in an atmosphere of low humidity. Conversely, if the amount of water is less than 3 parts by weight, a sheetlike absorbent material aimed at by this invention cannot be obtained. The amount of water is more desirably in the range of 5 to 25 parts by weight and most desirably in the range of 5 to 20 parts by weight, both based on 100 parts by weight of absorbent resin particles.

In the method for producing an absorbent material according with this invention, the water may be distilled water, deionized water, tap water, or industrial grade purified water. The water may have an inorganic substance or an organic substance dissolved or dispersed in advance therein.

In the method of production according with this invention, the amount of a polyhydric alcohol to be added to absorbent resin particles is in the range of 5 to 50 parts by weight based on 100 parts by weight. The absorbent resin particles in this case may contain therein a certain amount of the polyhydric alcohol on the condition that the resin particles should be effectively handled as a particulate substance in spite of the presence therein of the polyhydric alcohol. If the amount of the polyhydric alcohol exceeds 50 parts by weight, the absorbent material consequently obtained has a lower absorbent resin content and a smaller capacity for absorption. Conversely, if the amount of the polyhydric alcohol is less than 5 parts by weight, a sheetlike absorbent material capable of retaining high flexibility in spite of the effect of aging as aimed at by this invention cannot be obtained. The amount of the polyhydric alcohol is more desirably in the range of 5 to 40 parts by weight and most desirably in the range of 5 to 30 parts by weight, both based on 100 parts by weight of the absorbent resin particles.

This invention further provides a laminated absorbent material having a water-pervious sheet superposed on at least one surface of an absorbent material comprising 100 parts by weight of absorbent resin particles, 0.1 to 10 parts by weight of at least one absorption auxiliary selected from the group consisting of water-insoluble minute particles, surfactants, and fibers, 3 to 30 parts by weight of water, and 5 to 50 parts by weight of a polyhydric alcohol, which absorbent material is characterized by the fact that said absorbent material is in the form of a sheet having a thickness in the approximate range of about 0.3 to 5 mm and said form of a sheet results from mutual adhesion of the absorbent resin particles.

The details of the construction of this laminated absorbent material are identical to those of the laminated absorbent material described above.

The absorbent material and the laminated absorbent material of the present invention produce a supple and tough feeling, possess an ideal ability to absorb water, permits free section into pieces of desired size and shape, and therefore finds utility in various applications.

The absorbent material and the laminated absorbent material of this invention can be severally mixed with water-soluble macromolecular substances, deodorants, perfumes, medicines, plant growth accelerators, germicides, fungicides, foaming agents, pigments, carbon black, activated carbon, and filaments to give rise to absorbent materials which are vested with new functions.

The absorbent material of this invention can be combined with cellulose fibers or webs thereof or synthetic fibers or webs thereof to give rise to absorbent articles which ideally serve as absorbent layers in sanitary materials, for example. The production of such absorbent articles can be accomplished by a method suitably selected from among various known methods available for the manufacture of absorbent articles such as, for example, a method which comprises interposing an absorbent material between opposed sheets of paper, non-woven fabric, or mat made of cellulose fibers or synthetic fibers and a method which comprises blending cellulose fibers with ribbons of the absorbent material. Particularly, an absorbent article which has an absorbent material of this invention contained in a bag having at least one surface side thereof formed of a sheet pervious to water exhibits absorption properties comparable favorably with those of the conventional absorbent articles in spite of a smaller thickness and a compact size.

The absorbent material of this invention is a sheetlike absorbent material having a high speed of absorption and high flexibility and, unlike the conventional absorbent resin particles which are required to be incorporated at a relatively low concentration in a fibrous matrix for the purpose of preventing gel blocking, can be incorporated at a relatively high concentration in an absorbent article. To be specific, the absorbent article of this invention has an absorbent resin (substantially dry) content in the approximate range of 50 to 90% by weight based on the total weight of the absorbent article. The absorbent resin content is desirably in the approximate range of 60 to 90% by weight and more desirably in the approximate range of 70 to 90% by weight. Even when the absorbent article is manufactured with such a high resin concentration as mentioned above, the absorbent article neither permits the absorbent resin contained therein to migrate therein or spill therefrom nor suffers the feeling of its own to be degraded at the step of production of the absorbent article, the step of packaging, and the step of transportation because the absorbent material of this invention is in the form of a flexible sheet. Further the absorbent article excels in stability with which the physical properties thereof are retained in spite of the effect of aging until the absorbent article is put to use. Even when the absorbent article is left standing for a long time in an atmosphere of particularly low humidity, the high speed of absorption and flexibility can be retained intact.

Since the absorbent article of this invention is enabled to have a high absorbent resin content as described above, it is thin and compact in spite of the ability to absorb water which is favorably comparable with that of the conventional absorbent article. Owing to the high flexibility, this absorbent article fits the contour of the user's body satisfactorily and permits convenient handling.

The absorbent article of this invention is ideally used for absorbing numerous fluids including such bodily humors as urine, menstruous blood, and blood and can be applied to such products as disposable diapers, diapers intended for patients of incontinence, and pet pads, such sanitary articles as sanitary napkins and tampons, and such products as towels and bandages.

This invention further provides an absorbent article having an absorbent material contained in a bag having at least one surface side thereof formed of a water-permeable sheet, which absorbent material is in the form of a sheet comprising at least 60% by weight of absorbent resin and which absorbent article has the sheetlike absorbent material fixed thereto at 3 to 15 points per surface area of about 1,000 cm$^2$ of the sheetlike absorbent material.

Figure 2:
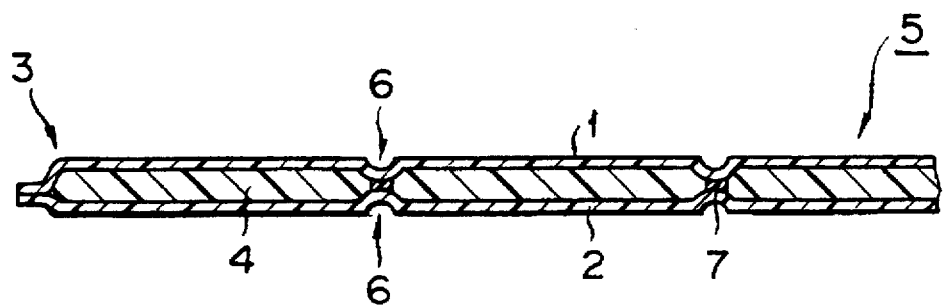
FIG. 2 is a cross section taken through FIG. 1 along the I—I line.

Specifically as illustrated in FIG. 1 and FIG. 2, an absorbent article 5 contain a sheetlike absorbent material 4 in a bag 3 having one surface thereof formed of a water-permeable sheet 1 and the other surface thereof formed of a water-impermeable sheet 2 or in a bag 3 having both surfaces thereof formed of water-permeable sheets 1 and 2.

This absorbent article 5 is furnished with point fixtures 6 at a prescribed number of positions per unit surface area of the sheetlike absorbent material 4. In this case, adhesive agent or thermoplastic resin 7 may be interposed between the opposite surfaces of the bag.

Figure 3:
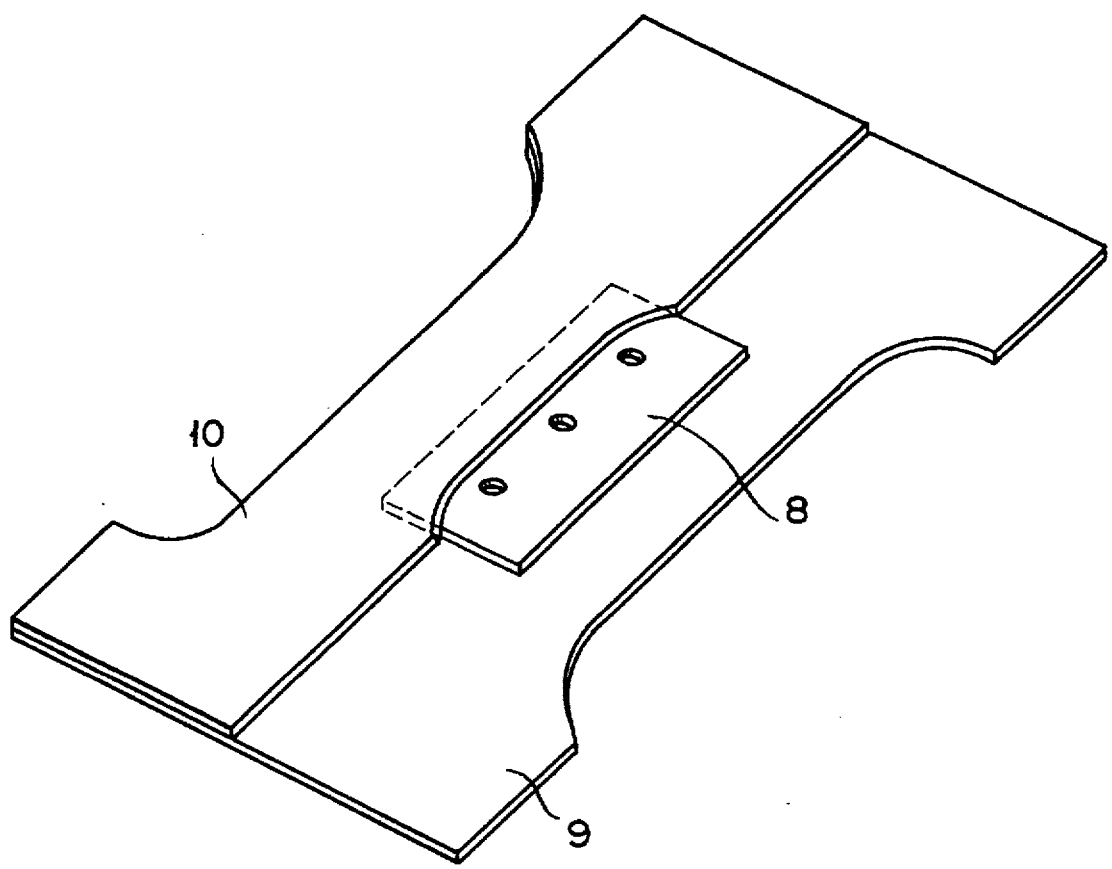
FIG. 3 is a partially cutaway perspective view illustrating the absorbent material according with this invention as used in a disposable diaper.

FIG. 3 illustrates an example of the application of an absorbent material 8 according with this invention to a disposable diaper which is obtained by inserting this absorbent material 8 between a back sheet 9 made of a water-impermeable sheet and a water-permeable sheet 10 such as, for example, non-woven fabric.

The absorbent material to be used for this invention is a sheetlike material comprising at least 60% by weight of absorbent resin. In order to obtain a thin absorbent article which is aimed at by this invention, it is necessary that an absorbent resin having a large capacity for absorption per unit weight as compared with paper or wood pulp fluff should be used at a high concentration. Further, for the purpose of preventing the absorbent resin from migration or maldistribution within the absorbent article while the absorbent article is in the process of packaging, transportation, storage, etc., it is necessary that the absorbent material should be in the form of a sheet.

The absorbent material which is used for this invention is desired to comprise absorbent resin particles and water and assume the form of a sheet resulting from mutual adhesion of the absorbent resin particles. More desirably, this absorbent material in the form of a sheet incorporates therein an absorption auxiliary as an additional component thereof. The details of the absorbent material of this composition have been already described. Owing to the use of the sheetlike absorbent material mentioned above, the absorbent resin can be prevented from migration and maldistribution within the absorbent article while the absorbent article is in the process of packaging, transportation, and storage prior to use. Further, since the amount of absorbent resin to be used per unit area of a given absorbent article is large, the absorbent article according with this invention is thin and compact while possessing absorption properties favorably comparable with those of the conventional absorbent articles.

In this invention, various substances can be used as a material for forming a bag. As typical examples of the substance, fibrous sheets such as of non-woven fabric, paper, woven fabric, and knit fabric and plastic sheets may be cited. Non-woven fabrics made of such synthetic resins as polyamide, polyesters, rayon, and acryl and woven fabrics and knit fabrics made of such synthetic resins as mentioned above, cotton, wool, hemp, jute, and wood are available. Optionally, a combination of two or more sheets may be used for the bag. At least one of the plurality of sheets thus used must be pervious to water.

The absorbent article according with this invention is furnished with 3 to 15 point fixtures per surface area of about 1,000 cm$^2$ of the sheetlike absorbent material made of absorbent resin. The term "point fixture" means an operation of fixing the opposed sheets forming the walls of the bag containing the sheetlike absorbent material either directly or through the medium of a certain amount of intervening matter at an indicated number of points each occupying a relatively narrow area (point adhesion, line adhesion, or narrow area adhesion) without giving rise to a whole area fixture or continuously fixed planes of wide area. The area of each point fixture is generally below 3 cm$^2$, preferably in the range of 0.05 to 2 cm$^2$, though variable with the position and number of point fixtures. The absorption resin, therefore, is omitted in advance from the positions allocated for point fixtures. When this omission is not made, the absorbent resin is not allowed to swell at the positions of point fixtures. The planes of such point fixtures are not discriminated by this invention on account of shape.

The number of these point fixtures is variable with the distribution of such point fixtures, the size of the bag, the shape of the bag because it is selected to meet the requirement that the sheetlike absorbent material contained in the bag should ensure the avoidance of deformation of the absorbent material while the absorbent article is in the process of actual use as aimed at by the present invention. By increasing the number of these point fixtures, the migration of gel inside the absorbent article while this article is in use can be repressed and the deformation of the absorbent material can be rendered more difficult to occur. The increase, however, lowers the capacity of the absorbent article for absorption. Surprisingly, even when this invention is applied to such an absorbent article as a disposable diaper which has a relatively large size, an absorbent article which possesses a large capacity for absorption, prevents migration of gel therein while in use, and avoids deformation as intended by this invention can be obtained with a relatively small number of point fixtures. The number of point fixtures is preferably in the range of 3 to 15, more desirably in the range of 4 to 13, and still more desirably in the range of 5 to 10 per a surface area of about 1,000 cm$^2$ of the sheetlike absorbent material.

Though the migration of gel in the adhesive article while the article is in use can be repressed and the deformation of the absorbent material rendered difficult to occur by increasing the number of point fixtures as described above, this addition decreases the capacity of the absorbent article for absorption. It has been found that the ratio of the maximum capacity of the bag for absorption (V ml) to the number of point fixtures (n), i.e. (V/n), is preferably in the range of 100 to 1,000, more preferably in the range of 100 to 500. If this ratio is less than 100, the capacity of the produced absorbent article is unduly small. If the ratio exceeds 1,000, the possibility arises that the migration of the gel resulting from absorption of liquid will not be thoroughly prevented.

This invention does not particularly discriminate the point fixtures on account of their positions. The point fixtures are suitably distributed, depending on the number of point fixtures, the size of the bag, and the shape of the bag. The distribution is selected to meet the requirement that the absorbent article should avoid deformation while in use as aimed at by this invention. Generally, it proves desirable though not invariably to select the positions of the point fixtures so that, when circles are drawn on the bag illustrated in a plan view around the point fixtures as centers with the shortest distances from the point fixtures to the edge of the bag as respective radiuses, the difference between the total of the areas of these circles (where the circles overlap, the overlapping areas will not be doubly counted) and the area of the bag shown in the plan view will be as small as permissible.

This invention does not particularly specify any method for the formation of point fixtures but permits use of any of the methods heretofore known to the art. A method which comprises directly fusing relevant portions of a given bag with heat or ultrasonic wave thereby joining the fused portions, a method which comprises effecting union of the relevant portions of a bag with the aid of adhesive agent, and a method which comprises interposing thermoplastic resin between the walls of a bag and thermocompressing the walls of the bag across the intervening thermoplastic resin at a temperature exceeding the softening point of the resin thereby giving rise to point fixtures through the medium of fused resin may be cited as concrete examples of the method usable for the formation of point fixtures.

The absorbent material and the laminated absorbent material of this invention produce supple and tough feeling, possess a highly satisfactory ability to absorb water, permit section into pieces of desired size and shape, and therefore find utility in various applications.

The absorbent material and the laminated absorbent material which are obtained in accordance with the methods of this invention, when necessary, may be mixed with water-soluble macromolecular substances, deodorants, perfumes, medicines, plant growth accelerators, germicides, fungicides, foaming agents, pigments, carbon black, activated carbon, filaments, etc. to give rise to absorbent materials vested with new functions.

When the absorbent material and the laminated absorbent material of this invention are combined with cellulose fibers or a web thereof or with synthetic fibers or a web thereof, they produce absorbent articles which serve as highly satisfactory absorbent layers in sanitary materials, for example. For the production of these absorbent articles, any of the means well known heretofore for the manufacture of absorbent articles such as, for example, a method which comprises sandwiching a given absorbent material between opposed sheets of paper, non-woven fabric, or mat made of cellulose fibers or synthetic fibers and a method which comprises preparing ribbons of cellulose fibers and ribbons of a given absorbent material and blending them together. Particularly, an absorbent article which has an absorbent material of this invention contained in a bag having at least one surface side thereof formed with a water-pervious sheet exhibits a capacity for absorption favorably comparable with that of the conventional absorbent article in spite of small thickness and volume.

The absorbent material and the laminated absorbent material of this invention are sheetlike absorbent materials which have a high speed of absorption and high flexibility and, unlike the conventional absorbent material which requires to incorporate absorbent resin particles in a fibrous matrix at a relatively low concentration for the purpose of preventing gel blocking, can be incorporated at a relatively high concentration in absorbent articles. Particularly noteworthy is the fact that the absorbent article of this invention has an absorbent resin (substantially dry) content in the approximate range of about 50 to 85% by weight based on the total weight of the absorbent article. The absorbent resin content is desirably in the approximate range of about 60 to 85% by weight and more desirably in the approximate range of about 70 to 85% by weight. In the absorbent article of this invention which is produced with such a high resin concentration as mentioned above, since this absorbent article is in the form of a flexible sheet, the absorbent resin neither migrates within the absorbent article nor spills therefrom possibly to the extent of jeopardizing the feeling of the absorbent article while the absorbent article is in the process of manufacture, packaging, and transportation.

The absorbent article of this invention is allowed to incorporate absorbent resins therein at such a high concentration as mentioned above, it is thin and compact while possessing a capacity for absorption favorably comparable with that of the conventional absorbent article. Because of high flexibility, the absorbent article well fits the contour of the user's body and ensures high convenience of use.

The absorbent article of this invention is ideally used for absorbing numerous fluids centering around such bodily humors as urine, menstrual blood, and blood and is applicable to such products as disposable diapers, diapers intended for patients of incontinence, and pet pads, sanitary articles such as sanitary napkins and tampons, and such products as towels and bandages.

EXAMPLES

Now, this invention will be described further below with reference to working examples. It should be noted, however, that this invention is not limited to these working examples. Referential Example 1 Example of synthesis of absorbent resin particles (A)

In a jacketed stainless steel kneader having an inner volume of 10 liters and provided with two sigma type vanes, 5,500 g of an aqueous solution of a monomer comprising 75 mol % of sodium acrylate and 25 mol % of acrylic acid (monomer concentration 38%) and 3.5 g of trimethylol propane triacrylate (0.05 g mol % based on the monomer) as a cross-linking agent were placed and nitrogen gas was blown to displace the air entrapped within the reaction system with nitrogen. The reactants in the kneader were heated by passing hot water at 35° C. through the jacket and meanwhile stirred by rotating the sigma type vanes at a rate of 40 r.p.m. and 2.8 g of sodium persulfate and 0.1 g of L-ascorbic acid were added as polymerization initiators to the stirred reactants to initiate polymerization of the monomer. The polymerization was continued for one hour. After the reaction was completed, the finely divided hydrogel polymer consequently formed was spread on a metallic net having meshes of 0.3 mm and was dried at 160° C. for one hour. The resultant dry mass (ppA) was ground by the use of a hammer mill and the produced particles were passed through a filter to obtain absorbent resin particles (A) minute enough to pass meshes of 850 μm. Of the absorbent resin particles (A), those which passed meshes of 150 μm accounted for 21% by weight based on the total amount of the particles (A).

Example 1

In a mold frame measuring 140 mm×100 mm, 10 g of the absorbent resin particles (A) were uniformly spread. The mold frame containing the spread resin particles (A) was left standing in a constant temperature constant humidity bath at 45° C. and a relative humidity of 80%. After 120 minutes' standing in the bath, an absorbent material (1) having a thickness of about 1.3 mm was obtained. By the gravimetric analysis, the absorbent resin particles (A) were found to have been given a water content of 3.8 g. The absorbent material consequently obtained was evaluated by the following methods. The results were as shown in Table 1.

A: Tensile yield strength and tensile yield elongation

These properties were determined by following the method of JIS (Japanese Industrial Standard) K7127 with necessary modifications.

Testing apparatus—Instron tester Model 4301
Test piece—Shape No. 5
Testing speed—200 mm/min.

B: Absorption capacity

A given absorbent material was sampled in an accurate amount of 0.5 g as reduced to absorbent resin particles. The sample was placed in a teabag-like pouch of non-woven fabric. The pouch containing the sample was kept immersed in an aqueous 0.9 wt % sodium chloride solution for 60 minutes. The wet pouch was then weighed. The absorption ratio was calculated in accordance with the following formula 1.

Absorption capacity (g/g)=(Weight (g) of packed pouch after the absorption−Weight (g) of a blank pouch)/0.5 (g)  (1)

C: Swelling speed

In a beaker having an inner volume of 100 ml, 50 ml of an aqueous 0.9 wt % sodium chloride solution and stirrer chips were stirred at a rate of 600 r.p.m. A given absorbent material was cut into cubes of about 1 cm. The cubes were sampled in an accurate amount of 2.0 g as reduced to absorbent resin particles. The sample was instantaneously thrown into the beaker and a stopwatch was started. The stopwatch was stopped at the time that the stirrer chips exposed in the central part of the swirl of the aqueous common salt solution were concealed by a swelled gel. The time interval thus found was reported as the speed of swelling. The length of this time interval decreases in proportion as the speed of swelling increases.

D: Water content

A given absorbent material was sampled accurately in an amount of 1.0 g. This sample was placed in an aluminum cup ($W_1$ g). The cup containing the sample was placed in a drier adjusted at 180° C. and left standing therein for three hours. The aluminum cup containing the sample was then removed from the drier and left cooled in a desiocator and weighed ($W_2$ g). In accordance with the following formula 2, the water content of the sample based on 100 parts by weight of substantially dry absorbent resin particles was calculated.

Water content=100·(1+$W_1$−$W_2$)/($W_2$−$W_1$)  (2)

E: Particle size distribution of absorbent resin particles

Classifying sieves of 16 mesh, 18.5 mesh, 30 mesh, 50 mesh, and 100 mesh according to the JIS standard mesh sizes were piled up on a receptacle. About 30 g of given absorbent resin particles were placed on the uppermost of the superposed sieves and shaken by a sieve shaker for 10 minutes. Then, the particles stopped on the sieves were weighed and their proportions to the total weight of the absorbent resin particles were reported in the denomination of % by weight based on the total weight of the absorbent resin particles used for the classification.

F: Absorption capacity under load of absorbent resin particles

The absorption capacity under load of given absorbent resin particles was determined by means of an apparatus illustrated in FIG. 4. An upper mouth 12 of a buret 11 was stoppered with a plug 13 and a measuring base 14 and an air inlet 15 were set flush with each other. A filter paper 17 was mounted on a glass fiber 16 with a diameter of 70 mm disposed in the central part of the measuring base 14.

Meanwhile, a piece of non-woven fabric 18 was fixed in the lower end part of a supporting cylinder 20 having a diameter of 55 m. On the non-woven fabric 18, 0.2 g of given absorbent resin particles were uniformly scattered and a load 19 of 20 g/cm$^2$ was further mounted. The superposed layers of non-woven fabric 18, absorbent resin particles 21, and load 19 as contained in the supporting cylinder 20 were mounted on the filter paper 17 overlying the glass filter 16. The amount of an aqueous 0.9 wt % sodium chloride solution (A ml) absorbed over a period of 30 minutes was measured. The absorption capacity under load was calculated by the following formula 3.

Absorption capacity under load (ml/g)=A (ml)/0.2 (g)  (3)

Example 2

In the same mold frame as used in Example 1, 10 g of the absorbent resin particles (A) were uniformly spread and moistened with 6.2 g of water applied thereto by the use of a spray. The whole mold frame containing the moistened absorbent resin particles was tightly sealed with a bag of polyethylene and left standing at 45° C. for 180 minutes. When the mold frame was removed from the bag, an absorbent material (2) about 1.4 mm in thickness was obtained. The absorbent material (2) was evaluated in the same manner as in Example 1. The results are shown in Table 1.

Example 3

An absorbent material (3) about 1.2 mm in thickness was obtained by following the procedure of Example 1, excepting the duration of standing in the bag was changed to 65 minutes. By the gravimetric analysis, it was found that the absorbent resin particles (A) had been given 2.0 g of water. The absorbent material (3) thus obtained was evaluated in the same manner as in Example 1. The results are shown in Table 1.

Control 1

The absorbent resin particles (A) were given 0.5 g of water by following the procedure of Example 1. They were very rigid and brittle and could not be easily handled as a sheet.

Control 2

The absorbent resin particles (A) were given 47 g of water by following the procedure of Example 2. They were very soft and brittle and could not be easily handled as a sheet.

Control 3

In the same mold frame as used in Example 1, 67 g of the absorbent resin particles (A) were uniformly spread and were wetted with 22 g of water by the use of a spray. The whole mold frame containing the moistened absorbent resin particles (A) was tightly sealed with a bag of polyethylene and left standing therein at 45° C. for 16 hours. When the mold frame was removed from the bag, a heterogeneous absorbent material (3a) for comparison about 8 mm in thickness was produced. The absorbent material (3a) for comparison thus obtained was evaluated in the same manner as in Example 1. The results are shown in Table 1.

Control 4

In a mixer, 10 g of the absorbent resin particles (A) were kept stirred and 3.8 g of water was added dropwise thereto. At once, lumps of a composition formed of the absorbent resins and water were obtained. These lumps had strong elasticity and could be torn into small pieces and could not be easily molded into a uniform sheet.

Control 5

The procedure of Example 1 was repeated, except that the absorbent resin particles (A) were used in an amount of 1.4 g (equivalent to a basis weight of 100 g/m$^2$). Lumps formed by partial conglomeration of particles were found. They could not be handled as an integral sheet.

Example 4

The absorbent resin particles (A) were passed through a sieve with meshes of 150 μm to separate absorbent resin particles (B) capable of passing a sieve with meshes of 150 µm. The absorbent resin particles (B) were given 3.8 g of water by following the procedure of Example 1, excepting the absorbent resin particles (B) were used instead. Consequently, an absorbent material (4) about 1.3 mm in thickness was obtained. The absorbent material (4) was evaluated in the same manner as in Example 1. The results are shown in Table 1.

Referential Example 2 Example of synthesis of absorbent resin particles (C)

In the same kneader as used in Referential Example 1, 1,100 g of acrylic acid, 2,500 g of an aqueous 2 wt % starch oxide solution, 1,850 g of water, and 2.7 g of N,N'-methylene bis-acrylamide (0.11 mol % based on the monomer) as a cross-linking agent were placed and nitrogen gas was blown to displace the air entrapped in the reaction system with nitrogen. With the contents of the kneader heated by passing water at 8° C. through the jacket and, at the same time, stirred by rotating the sigma type vanes at a rate of 40 r.p.m., 3.3 g of 2,2'-azo-bisamidinopropane dihydrochloride as a polymerization initiator, 0.3 g of L-ascorbic acid, and 3.1 g of an aqueous 35 wt % hydrogen peroxide solution were added to the kneader to initiate polymerization of the monomer. After the polymerization was initiated, the rotation of the sigma type vanes was stopped and the polymerization was continued for three hours. After this reaction was terminated, the sigma type vanes were set rotating at a rate of 40 r.p.m. to divide finely the produced hydrogel polymer. Then, the finely divided hydrogel polymer and 950 g of an aqueous 48 wt % sodium hydroxide solution added thereto were further stirred together by the rotating vanes. When the hydrogel polymer was caused to reach an elevated temperature of 86° C. by the heat of neutralization, the hydrogel polymer and an aqueous solution of 3.3 g of ethylene glycol diglycidyl ether as a cross-linking agent in 70 g of water added thereto were continuously stirred together by the rotation of the vanes. The produced hydrogel polymer was spread on a metallic net with meshes of 0.3 mm and then left drying thereon at 120° C. for three hours. The dry mass (ppC) consequently obtained was ground with a hammer mill to obtain absorbent resin particles (C) capable of passing a sieve of meshes of 850 µm. Of the absorbent resin particles (C), those which were capable of passing a sieve of meshes of 150 µm accounted for 25% by weight of the total weight of the absorbent resin particles (C).

Example 5

The absorbent resin particles (C) were given 3.6 g of water by following the procedure of Example 1, except that the absorbent resin particles (C) were used instead. An absorbent material (5) about 1.3 mm in thickness was consequently obtained. The absorbent material (5) was evaluated in the same manner as in Example 1. The results are shown in Table 1.

Example 6

The procedure of Example 1 was repeated, except that the absorbent resin particles were spread on a paper (A) measuring 140×100 mm (basis weight 15 g/m²) instead of the mold frame. A sheetlike article formed integrally of an absorbent material (1) about 1.3 mm in thickness and the paper (A) was obtained. A paper (A) identical with the paper (A) was superposed on the absorbent material (1) side of the sheetlike article and gently pressed down with a hand. Consequently, a laminated absorbent material having the absorbent material (1) sandwiched between the two papers (A) was obtained.

TABLE 1

|  | Example 1 Absorbent material (1) | Example 2 Absorbent material (2) | Example 3 Absorbent material (3) | Example 4 Absorbent material (4) | Example 5 Absorbent material (5) |
|---|---|---|---|---|---|
| Water content (parts by weight)* | 45 | 70 | 26 | 47 | 51 |
| Tensil yield strength (kg/cm²) | 14 | 7 | 5 | 16 | 13 |
| Tensil yield elongation (%) | 360 | 700 | 150 | 400 | 250 |
| Absorption capacity (g/g) | 48 | 48 | 48 | 48 | 41 |
| Swelling speed (sec) | 45 | 60 | 42 | 2 | 53 |

|  | Control 1 | Control 2 | Control 3 Absorbent material for comparison (3a) |
|---|---|---|---|
| Water content (parts by weight)* | 10 | 500 | 40 |
| Tensil yield strength (kg/cm²) | — | — | 1 |
| Tensil yield elongation (%) | — | — | 7 |
| Absorption ratio (g/g) | 48 | 48 | 47 |
| Swelling speed (sec) | — | — | 95 |

*Water content based on 100 parts by weight of substantially dry absorvent resin particles Referential Example 3 Example of synthesis of absorbent resin particles (D)

The absorption resin particles (A) obtained in Referential Example 1 were found to have an absorption capacity under load of 16 ml/g. One hundred (100) parts by weight of the absorbent resin particles (A) were mixed with an aqueous mixture comprising 0.5 part by weight of glycerol, 3 parts by weight of water, and 2 parts by weight of isopropanol. The resultant mixture was placed in a bowl immersed in an oil bath (195° C.) and stirred and heat-treated for 40 minutes to obtain absorbent resin particles (D) capable of passing a sieve of meshes of 850 µm. Of the absorbent resin particles (D), those which were capable of passing a sieve of meshes of 150 µm accounted for 13% by weight based on the total weight of the absorbent resin particles (D). The absorbent resin particles (D) were found to have an absorption capacity under load of 26 ml/g.

Example 7

In a mold frame measuring 150 mm×200 mm, 15 g of the absorbent resin particles (A) were uniformly spread. As a result, the absorbent resin particles (A) were spread in the form of a planar layer about 0.7 mm in thickness. The planar layer was left standing in a constant temperature constant humidity bath kept at 45° C. and a relative humidity of 80%. After 120 minutes standing in the bath, an absorbent material (7) in the form of a sheet was obtained. The absorbent particles (A) were found to have been given 5.7 g of water. The absorbent material (7) was evaluated in the same manner as in Example 1 and additionally by the following methods. The results are shown in Table 2.

G: Speed of absorption

A given absorbent material was cut to obtain a square of 45 mm. This square sample was placed in a cylindrical container having a bottom surface 6 cm in diameter and placed on a horizontal base. Onto the square sample, 20 g of artificial urine at 22° C. was added all at once. At the same time, a stopwatch was started. The artificial urine was composed of 2.0 g of KCl, 2.0 g of $Na_2SO_4$, 0.85 g of $(NH_4)_2HPO_4$, 0.15 g of $(NH_4)_2HPO_4$, 0.19 g of $CaCl_2$, and 0.23 g of $MgCl_2$ severally per liter. The stopwatch was stopped at the moment that the artificial urine was absorbed completely by the absorbent material. The time interval thus found was reported as the speed of absorption. The length of the time interval decreases in proportion as the speed of absorption increases.

H: Flexibility

A given absorbent material having a width of at least 2 cm was placed horizontally and, with one half of the absorbent material kept in a flat plane, the absorbent material was gently rotated about a straight line dividing the surface area of the absorbent material into two substantially equal parts. The angle produced by this rotation from the horizontal plane by the time the absorbent material sustained a substantial crack was reported as the flexibility. The angle increases in proportion as the flexibility increases.

Example 8

In a mold frame measuring 150 mm×200 mm, 15 g of the absorbent resin particles (D) were uniformly spread. As a result, the absorbent resin particles (D) were spread in the form of a planar layer about 0.7 mm in thickness. The planar layer was left standing in a constant temperature constant humidity bath kept at 45° C. and a relative humidity of 80%. After 150 minutes' standing in the bath, a sheetlike absorbent material (8) was obtained. The absorbent resin particles (D) were found to have been given 6.1 g of water. The absorbent material (8) was evaluated in the same manner as in Example 7. The results are shown in Table 2.

Example 9

Fifteen (15) g of the absorbent resin particles (D) was mixed with 0.15 g of water-insoluble finely divided silica (produced by Japan Aerosil Ltd. and marketed under trademark designation of "Aerosil 200"). The resultant mixture was spread uniformly in a mold frame measuring 150 mm×200 mm. As a result, the mixture of absorbent resin particles (D) with finely divided silica was spread in the form of a planar layer about 0.7 mm in thickness. This planar layer was left standing in a constant temperature constant humidity bath kept at 45° C. and a relative humidity of 80%. After 150 minutes' standing in the bath, the planar layer produces an absorbent material (9) in the form of a sheet. The absorbent resin particles (D) were found to have been given 6.2 g of water. The absorbent material (9) was evaluated in the same manner as in Example 7. The results are shown in Table 2.

Referential Example 5 Example of synthesis of absorbent resin particles (E)

A cylindrical separable flask having an inner volume of 500 ml was charged with an aqueous monomer solution composed of 8.6 g of sodium salt of 2-sulfoethyl methacrylate, 35.4 g of acrylic acid having 75 mol % thereof neutralized with a sodium salt, 0.077 g of trimethylol propane triacrylate (0.06 mol % based on the monomer) as a cross-linking agent, and 69 g of water. The mixture in the flask was stirred and the air entrapped in the reaction system was displaced with nitrogen and the temperature of the aqueous monomer solution was adjusted to 30° C. Then, the aqueous monomer mixture was combined with 0.5 g of an aqueous 10% sodium persulfate and 0.4 g of an aqueous 0.5% L-ascorbic acid solution. The stirring was discontinued and the polymerization of the monomer was initiated. In 15 minutes after the initiation of polymerization, the internal temperature of the reaction system rose to 70° C. After the start of the drop of the internal temperature was confirmed, the polymerization system was externally heated to 75° C. and kept at this temperature for one hour. The hydrogel polymer consequently obtained was finely divided and dried at 150° C. for 90 minutes. The dry mass (ppE) consequently obtained was ground with a hammer mill to obtain absorbent resin particles (pE) capable of passing a sieve of meshes of 300 μm. One hundred (100) parts by weight of the absorbent resin particles (pE) was mixed with an aqueous mixture comprising 1 part by weight of glycerol, 1 part by weight of water, and 2 parts by weight of isopropanol. The resultant mixture was placed in a bowl immersed in an oil bath (195° C.) and stirred and heat-treated therein for 30 minutes to obtain absorbent resin particles (E) capable of passing a sieve of meshes of 300 μm. Of the absorbent resin particles (E), those capable of passing a sieve of meshes of 150 μm accounted for 27% by weight based on the total amount of the absorbent resin particles (E). The absorbent resin particles (E) were found to have an absorption capacity under load of 24 ml/g.

Example 10

In a mold frame measuring 150 mm×200 mm, 15 g of the absorbent resin particles (E) were uniformly spread. As a result, the absorbent resin particles (E) were spread in the form of a planar layer about 0.7 mm in thickness. They were given 5.9 g of water by spraying. Consequently, an absorbent material (10) in the form of a sheet was obtained. The absorbent material (10) was evaluated in the same manner as in Example 7. The results are shown in Table 2.

Example 11

Fifteen (14) g of the absorbent resin particles (E) were mixed with 0.15 g of water-insoluble finely divided silica (produced by Japan Aerosil Ltd. and marketed under trademark designation of "Aerosil 200"). The resultant mixture was uniformly spread in a mold frame measuring 150 mm×200 mm. As a result, the mixture of the absorbent resin particles (E) with the finely divided silica was spread in the form of a planar layer. The planar layer was given 6.2 g of water by spraying to give rise to an absorbent material (11) in the form of a sheet. The absorbent material (11) thus obtained was evaluated in the same manner as in Example 7. The results are shown in Table 2.

Example 12

The absorbent resin particles (E) obtained in Referential Example 5 were classified with a sieve of meshes of 150 μm to obtain absorbent resin particles (F) which are capable of passing sieves of meshes of 300 μm to 150 μm. The absorbent resin particles (F) were found to have an absorption ratio under load of 28 ml/g. An absorbent material (12) in the form of a sheet was obtained by repeating the procedure of Example 10, excepting the absorbent resin particles (F) were used instead. The absorbent material (12) thus obtained was evaluated in the same manner as in Example 7. The results are shown in Table 2.

Control 6

By following the procedure of Example 8, the absorbent resin particles (D) uniformly spread in a mold frame were left standing in a constant temperature constant humidity bath kept at 45° C. and a relative humidity of 80%. After 100 minutes' standing in the bath, the mold frame was removed from the bath and the upper surface of a wet layer of the absorbent resin particles (D) was rubbed with a metallic pestle. Then, the layer of the absorbent resin particles (D) held in the mold frame was left standing in the constant temperature constant humidity bath for 50 minutes. It was subsequently removed from the bath and the upper surface of the layer of the absorbent resin particles (D) was again rubbed with the metallic pestle. Thus, the absorbent resin particles (D) were found to have been given 6 g of water. An absorbent material (6c) for comparison consequently obtained was evaluated in the same manner as in Example 7. The results are shown in Table 2.

absorbent resin particles (D). Though part of the particles were found to have been conglomerated into lumps, the particles persisted in a particulate form and failed to form a sheet.

Example 13

The procedure of Example 9 was repeated, except that 0.75 g of cellulose powder (produced by Sanyo Kokusaku Pulp Co., Ltd. and marketed under trademark designation of "KC floe W-300") was used in the place of 0.15 g of the water-insoluble finely divided silica (produced by Japan Aerosil Ltd. and marketed under trademark designation of "Aerosil 200"). Thus, the absorbent resin particles (D) were given 6.2 g of water. An absorbent material (13) consequently obtained was evaluated in the same manner as in Example 7. The results are shown in Table 2.

TABLE 2

| | Example 7 | Example 8 | Example 9 | Example 10 | Example 11 | Example 12 | Example 13 |
|---|---|---|---|---|---|---|---|
| Water content (parts by weight) | 45 | 41 | 41 | 39 | 41 | 39 | 41 |
| Absorption auxiliary content (parts by weight) | 0 | 0 | 1 | 0 | 1 | 0 | 5 |
| Absorption capacity (g/g) | 48 | 42 | 44 | 40 | 42 | 40 | 42 |
| Speed of absorption (sec) | 120 | 40 | 8 | 75 | 6 | 18 | 18 |
| Flexibility (degrees) | >180 | >180 | >180 | >180 | >180 | >180 | >180 |

| | Control 6 | Control 7 | Control 8 | Control 9 |
|---|---|---|---|---|
| Water content (parts by weight) | 41 | 40 | 5 | 40 |
| Absorption auxiliary content (parts by weight) | 0 | 0 | 0 | 1 |
| Absorption capacity (g/g) | 42 | Sheet did not form | Sheet did not form | Sheet did not form |
| Speed of absorption (sec) | 140 | | | |
| Flexibility (degrees) | >180 | | | |

Control 7

In a mixer, 15 g of the absorbent resin particles (E) were stirred and 6 g of water was added dropwise to the stirred resin particles. Immediately, lumps of a composition of the absorbent resin and water were obtained. They possessed strong elasticity and could be torn into small pieces. They could not easily form a uniform sheet.

Control 8

The procedure of Example 8 was repeated, except that the absorbent resin particles (D) were given 0.8 g of water. Though part of the particles were found to have been conglomerated into lumps, the particles persisted in a particulate form and failed to form a sheet.

Control 9

The procedure of Example 9 was followed, except that 4.2 g of the absorbent resin particles (D) were mixed with 0.04 g of water-insoluble finely divided silica (produced by Japan Aerosil Ltd. and marketed under trademark designation of "Aerosil 200") and the resultant mixture was uniformly spread in a mold frame measuring 150 mm×200 mm. The layer of the mixer in the mold frame was left standing in a constant temperature constant humidity bath kept at 45° C. and a relative humidity of 80% to give 1.7 g of water to the Example 14

The procedure of Example 7 was repeated, except that a paper measuring 150 mm×300 mm (produced by Nangoku Pulp Industry Co., Ltd. and marketed under trademark designation of "Heation Paper GS22") spread on a horizontal base was used in the place of the mold frame. Consequently, a laminated sheet having an absorbent material about 0.5 mm in thickness superposed on the paper was produced. Separately, in a commercially available disposable diaper (produced by Shiseido Co., Ltd. and marketed under trademark designation of "Pingpong Pant L size"), a waterproof sheet of polyethylene film was cut longitudinally along the center line and an absorbent member formed of absorbent resin, fluffy pulp, and absorbent paper was removed through the cut from the disposable diaper. The laminated sheet mentioned above was incorporated in the chassis of the disposable diaper in such a manner that the absorbent material would fall on the surface member (nonwoven fabric of polypropylene) side of the chassis, with the cut in the waterproof sheet closed with an adhesive tape. An absorbent article (1) consequently obtained was evaluated by the following method. The results are shown in Table 3.

I: Method for evaluation of absorbent article

A baby model provided with a ureter was prepared by imitating an infant weighing 10 kg. The absorbent article (1) produced in Example 14 was put on the baby model and artificial urine was discharged through the ureter at a speed of 50 ml/10 sec. into the absorbent article (1). The same urination was repeated after an interval of 50 minutes. The amount of the artificial urine absorbed by the absorbent article (1) until the artificial urine began to leak therefrom was used for evaluating the article's proofness against leakage of urine.

Examples 15 to 19

Laminate sheets each having an absorbent material superposed on Heation Paper GS22 were produced by repeating the procedure of Example 14, except that the respective absorbent materials were produced by following the procedures of Examples 8 to 12. Then, absorbent articles (2 to 6) were obtained by repeating the procedure of Example 14. The absorbent articles (2 to 6) were evaluated in the same manner as in Example 14. The results are shown in Table 3.

Control 10

A sheet having the absorbent resin particles (D) superposed thereon was produced by repeating the procedure of Example 14, except that the production of an absorbent material was effected by repeating the procedure of Control 8. The absorbent resin particles (D) were fixed sparingly and were not very easily handled. By subjecting the sheet supporting the absorbent resin particles (D) to the procedure of Example 14 thereafter, an absorbent article (1c) for comparison was obtained. The absorbent article (1c) for comparison thus obtained was evaluated in the same manner as in Example 14. The results are shown in Table 3. The absorbent resin particles were observed to migrate and disperse unevenly within the absorbent article (1c) for comparison.

TABLE 3

|  | Example 14 | Example 15 | Example 16 | Example 17 | Example 18 | Example 19 |
|---|---|---|---|---|---|---|
| Absorbent article | (1) | (2) | (3) | (4) | (5) | (6) |
| Absorption capacity of absorbent article (ml) | 150 | 300 | 350 | 250 | 350 | 350 |

|  | Control 10 |
|---|---|
| Absorbent article | Comparison (1c) |
| Absorption capacity of absorbent article (ml) | 100 |

Referential Example 6 Example of synthesis of absorbent resin particles (G)

In a jacketed kneader of stainless steel having an inner volume of 10 liters and provided with two sigma type vanes, 5,500 g of the aqueous solution of a monomer (monomer concentration 38%) composed of 75 mol % of sodium acrylate and 25 mol % of acrylic acid and 4.2 g of trimethylol propane triacrylate (0.06 mol % based on the monomer) were placed and nitrogen gas was blown to displace the air entrapped in the reaction system with nitrogen. With the contents of the kneader heated by passing hot water at 35° C. through the jacket and, at the same time, stirred by rotating the sigma type vanes at a rate of 40 r.p.m., the monomer was set polymerizing by the addition of 2.8 g of sodium persulfate as a polymerization initiator and 0.1 g of L-ascorbic acid. The polymerization reaction was continued for one hour. After the reaction was completed, a finely divided hydrogel polymer consequently obtained was spread on a metallic net of meshes of 0.3 mm and then dried at 160° C. for one hour. The dry mass (ppG) consequently obtained was ground with a hammer mill to obtain absorbent resin particles (pG) capable of passing a sieve of meshes of 850 µm. Of the absorbent resin particles (pG), those which were capable of passing a sieve of meshes of 150 µm accounted for 18% by weight based on the total amount of the absorbent resin particles (pG). The absorbent resin particles (pG) were found to have an absorption capacity under load of 16 ml/g. One hundred (100) parts by weight of the absorbent resin particles (pG) were mixed with an aqueous mixture composed of 0.5 part by weight of glycerol, 2 parts by weight of water, and 2 parts by weight of isopropanol. The resultant mixture was placed in a bowl immersed in an oil bath (195° C.) and stirred and heat-treated therein for 40 minutes to obtain absorbent resin particles (G). Of the absorbent resin particles (G), those which were capable of passing a sieve of meshes of 150 µm accounted for 15% by weight based on the total weight of the absorbent resin particles (G). These absorbent resin particles (G) were found to have an absorption capacity under load of 28.5 ml/g.

Example 20

Fifteen (15) g of the absorbent resin particles (pG) was mixed with 0.15 g of water-insoluble finely divided silica (produced by Japan Aerosil Ltd. and marketed under trademark designation of "Aerosil 200"). The resultant mixture was spread uniformly in a mold frame measuring 150 mm×200 mm. By spraying 3.9 g of an aqueous 50 wt % glycerol solution onto the planar layer of the absorbent resin particles (pG), a sheetlike absorbent material (20) about 0.8 mm in thickness was obtained. The absorbent material (20) was evaluated by the method described in Example 1 and Example 7. The results are shown in Table 4. It was tested for speed of absorption and flexibility, both with aging, by the following methods.

J: Speed of absorption with aging

A given absorbent material was cut to obtain a square of 45 mm. This square sample was left standing in a constant temperature constant humidity bath kept at 25° C. and a relative humidity of 40% for 180 minutes. The absorbent material removed from the constant temperature constant humidity bath was tested by the method of G mentioned above. The time interval determined by the test was reported as the speed of absorption with aging. The length of this interval decreases in proportion as the speed of absorption with aging increases.

K: Flexibility with aging

A given absorbent material having a width of at least 2 cm was left standing in a constant temperature constant humidity bath kept at a relative humidity of 40% for 180 minutes. The absorbent material removed from the constant temperature constant humidity bath was tested by the method of H mentioned above. The angle formed by the rotation from the horizontal plane by the time that the absorbent material sustained a substantial crack was reported as the flexibility with aging. The angle increases in proportion as the degree of flexibility with aging increases.

Example 21

Fifteen (15) g of the absorbent resin particles (G) were mixed with 0.15 g of water-insoluble finely divided silica (produced by Japan Aerosil Ltd. and marketed under trademark designation of "Aerosil 200"). The resultant mixture was spread uniformly in a mold frame measuring 150 mm×200 mm. A sheetlike absorbent material (21) about 0.8 mm in thickness was obtained by spraying 4.0 g of an aqueous solution containing glycerin at a concentration onto the layer of the absorbent resin particles (G) in the mold frame. The absorbent material (21) was evaluated in the same manner as in Example 20. The results are shown in Table 4.

Example 22

The absorbent resin particles (G) were classified with a metallic net with meshes of 150 μm to obtain absorbent resin particles (H) which were capable of passing sieves of meshes of 850 μm to 150 μm. Fifteen (15) g of the absorbent resin particles (H) were mixed with 0.15 g of water-insoluble finely divided silica (produced by Japan Aerosil Ltd. and marketed under trademark designation of "Aerosil 200"). The resultant mixture was uniformly spread on a mold frame measuring 150 mm×200 mm onto which 1.8 g of an aqueous solution containing glycerol at a concentration of 50% by weight had been sprayed in advance. By further spraying 1.8 g of an aqueous solution containing glycerin at a concentration of 50% by weight, a sheetlike absorbent material (22) about 0.8 mm in thickness was obtained. The absorbent material (22) was evaluated in the same manner as in Example 20. The results are shown in Table 4.

Example 23

Fifteen (15) g of the absorbent resin particles (E) were mixed with 0.3 g of water-insoluble finely divided silica (produced by Deggusa K.K. and marketed under trademark designation of "Siebelnat 22S"). The resultant mixture was uniformly spread in a mold frame measuring 150 mm×200 mm. A sheetlike absorbent material (23) about 0.8 mm in thickness was obtained by spraying 4.8 g of an aqueous solution containing glycerol at a concentration of 50% by weight onto the layer of the absorbent resin particles (E) in the mold frame. The absorbent material (23) was evaluated in the same manner as in Example 20. The results are shown in Table 4.

Example 24

The absorbent resin particles (E) were classified with a sieve of meshes of 150 μm to obtain absorbent resin particles (I) which were capable of passing a sieve of meshes of 150 μm. A sheetlike absorbent material (24) about 0.8 mm in thickness was obtained by repeating the procedure of Example 23, except that the absorbent resin particles (I) were used instead. The absorbent material (24) was evaluated in the same manner as in Example 20. The results are shown in Table 4.

Example 25

A sheetlike absorbent material (25) about 0.9 mm in thickness was obtained by repeating the procedure of Example 23, except that 0.75 g of cellulose powder (produced by Sanyo Kokusaku Pulp Co., Ltd. and marketed under trademark designation of KC Floe W-300") was used in the place of 0.3 g of the water-insoluble finely divided silica (produced by Deggusa K.K. and marketed under trademark designation of "Siebelnat 22S"). The absorbent material (25) was evaluated in the same manner as in Example 20. The results are shown in Table 4.

Example 26

A sheetlike absorbent material (26) was obtained by repeating the procedure of Example 21, except that 6.0 g of an aqueous solution containing glycerol at a concentration of 75% by weight was used for the purpose of spraying in the place of 4.0 g of the aqueous solution containing glycerol at a concentration of 50% by weight. The absorbent material (26) was evaluated in the same manner as in Example 20. The results are shown in Table 4.

Example 27

A paper (a) measuring 150 mm×200 mm (basis weight 15 g/m$^2$) was spread on a horizontal base. On the flat paper (a), a mixture of 15 g of the absorbent resin particles (G) with 0.15 g of water-insoluble finely divided silica (produced by Japan Aerosil Ltd. and marketed under trademark designation of "Aerosil 200") was uniformly spread. A sheet having superposed thereon a sheetlike absorbent material about 0.8 mm in thickness was produced by spraying 2.0 g of an aqueous solution containing glycerol at a concentration of 50% by weight onto the uniformly spread mixture. Another paper (a) of the same size was superposed on the absorbent material and the resultant laminate was superposed on a metallic net of 16 mesh (JIS). The laminate on the metallic net was kept under a pressure of 3 kg/cm$^2$ for three minutes to obtain a laminated absorbent material (27) having an absorbent material sandwiched between the papers (a). The laminated absorbent material (27) was evaluated in the same manner as in Example 20. The results are shown in Table 4.

TABLE 4

| | Example 20 | Example 21 | Example 22 | Example 23 |
|---|---|---|---|---|
| Absorption auxiliary content (parts by weight) | 1 | 1 | 1 | 2 |
| Water content (parts by weight) | 19 | 13 | 12 | 16 |
| Polyhydric alcohol content (parts by weight) | 13 | 13 | 12 | 16 |
| Absorbent material | (20) | (21) | (22) | (23) |
| Absorption capacity (g/g) | 44 | 41 | 41 | 42 |
| Speed of absorption (sec) | 102 | 22 | 49 | 14 |
| Speed of absorption with aging (sec) | 114 | 26 | 55 | 15 |
| Flexibility (degrees) | >180 | >180 | >120 | >180 |
| Flexibility with aging (degrees) | >120 | >180 | >120 | >180 |

| | Example 24 | Example 25 | Example 26 | Example 27 |
|---|---|---|---|---|
| Absorption auxiliary content (parts by weight) | 2 | 5 | 1 | 1 |
| Water content (parts by weight) | 16 | 16 | 10 | 7 |
| Polyhydric alcohol content (parts by weight) | 16 | 16 | 30 | 7 |
| Absorbent material | (24) | (25) | (26) | Laminate (27) |
| Absorption capacity (g/g) | 42 | 41 | 41 | 41 |
| Speed of absorption (sec) | 8 | 15 | 30 | 25 |
| Speed of absorption with aging (sec) | 8 | 18 | 32 | 28 |
| Flexibility (degrees) | >180 | >180 | >180 | >180 |
| Flexibility with aging (degrees) | >180 | >120 | >180 | >180 |

Example 28

A sheetlike absorbent material (28) about 0.8 mm in thickness was obtained by repeating the procedure of Example 21, except that an aqueous ethylene glycol solution was used in the place of the aqueous glycerin solution. The absorbent material (28) was evaluated in the same manner as in Example 20. The results are shown in Table 5.

Example 29

A sheetlike absorbent material (29) about 0.8 mm in thickness was obtained by repeating the procedure of Example 21, except that an aqueous diethylene glycol solution was used in the place of the aqueous glycerol solution. The absorbent material (29) was evaluated in the same manner as in Example 20. The results are shown in Table 5.

Example 30

A sheetlike absorbent material (30) about 0.8 mm in thickness was obtained by repeating the procedure of Example 21, except that 5.3 g of an aqueous 28 wt % glycerol solution was used in the place of 4.0 g of the aqueous 50 wt % glycerin solution. The absorbent material (30) was evaluated in the same manner as in Example 20. The results are shown in Table 5.

Control 11

Fifteen (15) g of the absorbent resin particles (G) were mixed with 0.15 g of water-insoluble finely divided silica (produced by Japan Aerosil Ltd. and marketed under trademark designation of "Aerosil 200"). The resultant mixture was further mixed with 1.8 g of glycerol. The mixture consequently obtained was spread in a mold frame measuring 150 mm×200 mm but failed to form a sheet.

Control 12

No sheet was formed when the procedure of Example 21 was repeated, except that 0.6 g of an aqueous 75 wt % glycerin solution was used in the place of 4.0 g of the aqueous 50 wt % glycerol.

Control 13

A sheetlike absorbent material (13c) for comparison about 0.8 mm in thickness was obtained by repeating the procedure of Example 23, except that the use of the water-insoluble finely divided silica was omitted. The absorbent material (13c) for comparison was evaluated in the same manner as in Example 20. The results are shown in Table 5.

Control 14

In a mixer, a mixture of 15 g of the absorbent resin particles (G) with 0.15 g of water-insoluble finely divided silica (produced by Japan Aerosil Ltd. and marketed under trademark designation of "Aerosil 200") was kept stirred and 4.0 g of an aqueous 50 wt % glycerol solution was added dropwise to the stirred mixture. The operation immediately gave rise to lumps of a composition of the absorbent resin, water, and glycerol. Though the lumps possessed strong elasticity and could be torn into small pieces, they did not easily form a uniform sheet.

Control 15

A mixture containing of 4.2 g of the absorbent resin particles (G) and 0.04 g of water-insoluble finely divided silica (produced by Japan Aerosil Ltd. and marketed under trademark designation of "Aerosil 200") was prepared. This mixture was uniformly spread in a mold frame measuring 150 mm×200 mm. When 1.1 g of an aqueous 50 wt % glycerol solution was sprayed on the spread layer of the absorbent resin particles in the mold frame, part of the particles were found to have formed lumps and the whole particles failed to form a sheet.

TABLE 5

| | Example 28 | Example 29 | Example 30 | Control 11 |
|---|---|---|---|---|
| Absorption auxiliary content (parts by weight) | 1 | 1 | 1 | 1 |
| Water content (parts by weight) | 13 | 13 | 25 | 0 |
| Polyhydric alcohol content (parts by weight) | 13 | 13 | 10 | 12 |
| Absorbent material | (28) | (29) | (30) | Sheet did not form |
| Absorption capacity (g/g) | 41 | 41 | 41 | |
| Speed of absorption (sec) | 23 | 25 | 21 | |
| Speed of absorption with aging (sec) | 25 | 25 | | |
| Flexibility (degrees) | >180 | >180 | >180 | |
| Flexibility with aging (degrees) | >180 | >180 | 40> | |

| | Control 12 | Control 13 | Control 14 | Control 15 |
|---|---|---|---|---|
| Absorption auxiliary content (parts by weight) | 1 | 0 | 1 | 1 |
| Water content (parts by weight) | 1 | 16 | 13 | 13 |
| Polyhydric alcohol content (parts by weight) | 3 | 16 | 13 | 13 |
| Absorbent material | | Comparison (13c) | | |
| Absorption capacity (g/g) | Sheet did not form | 40 | Sheet did not form | Sheet did not form |
| Speed of absorption (sec) | | 110 | | |
| Speed of absorption with aging (sec) | | 115 | | |
| Flexibility (degrees) | | >180 | | |
| Flexibility with aging (degrees) | | >180 | | |

Example 31

The procedure of Example 20 was repeated, except that a paper measuring 150 mm×300 mm (produced by Nangoku Pulp Industry Co., Ltd. and marketed under trademark designation of Heatlon Paper GS22") and spread on a horizontal base was used in the place of the mold frame, to obtain a laminated sheet having superposed on the Heatlon Paper GS22 an aqueous material about 0.5 mm in thickness. Separately, in a commercially available disposable diaper (produced by Shiseido Co., Ltd. and marketed under trademark designation of "Pingpong Pant L size"), a waterproof sheet of polyethylene film was cut longitudinally along the center line and an absorbent member formed of absorbent resin, fluffy pulp, and absorbent paper was removed through the cut from the disposable diaper. The aforementioned sheet was incorporated in the chassis of the disposable diaper in such a manner that the absorbent material would fall on the surface member (non-woven fabric of polypropylene) side of the chassis, with the cut in the waterproof sheet closed with an adhesive tape. An absorbent article (7) consequently obtained was evaluated by the following method. The results are shown in Table 6.

Examples 32 to 35

Laminate sheets each having an absorbent material superposed on Heatlon Paper GS22 were produced by repeating the procedure of Example 31, except that the respective absorbent materials were produced by following the procedures of Examples 21 to 24. Then, absorbent articles (8 to 11) were obtained by repeating the procedure of Example 14. The absorbent articles (8 to 11) were evaluated in the same manner as in Example 31. The results are shown in Table 6.

Control 16

A sheet having the absorbent resin particles (G) superposed thereon was produced by repeating the procedure of Example 31, except that the production of an absorbent material was effected by repeating the procedure of Control 11. The absorbent resin particles (G) were fixed sparingly and were not very easily handled. By subjecting the sheet supporting the absorbent resin particles (G) to the procedure of Example 31 thereafter, an absorbent article (2c) for comparison was obtained. The absorbent article (2c) for comparison thus obtained was evaluated in the same manner as in Example 31. The results are shown in Table 6. The absorbent resin particles were observed to migrate and disperse unevenly within the absorbent article (2c) for comparison.

TABLE 6

|  | Example 31 | Example 32 | Example 33 | Example 34 | Example 35 | Control 16 |
|---|---|---|---|---|---|---|
| Absorbent article | (7) | (8) | (9) | (10) | (11) | Comparison (2c) |
| Absorption Capacity of absorbent article (ml) | 150 | 350 | 300 | 300 | 250 | 100 |

Example 36

Fifteen (15) g of the absorbent resin particles (D) were mixed with 0.15 g of water-insoluble finely divided silica (produced by Japan Aerosil Ltd. and marketed under trademark designation of "Aerosil 100"). The resultant mixture was uniformly spread on a paper measuring 150 mm×300 mm (produced by Nangoku Pulp Industry Co., Ltd. and marketed under trademark designation of "Heatlon Paper GS22") and spread on a horizontal base. A sheet (1) having superposed thereon a sheetlike absorbent material was produced by spraying 6 g of water onto the spread mixture on the paper. On a rectilinear line dividing the sheet (1) longitudinally into two equal halves, circles 15 mm in diameter were punched out one each around three points dividing the rectilinear line into four equal lengths. Separately, in a commercially available disposable diaper (produced by Shiseido Co., Ltd. and marketed under trademark designation of "Pingpong Pant L size"), a waterproof sheet of polyethylene film was cut longitudinally along the center line and an absorbent member formed of absorbent resin, fluffy pulp, and absorbent paper was removed through the cut from the disposable diaper. The aforementioned sheet (1) was incorporated in the chassis of the disposable diaper in such a manner that the absorbent material would fall on the surface member (non-woven fabric formed of polypropylene) side of the chassis. In this case, the leading end of the sheet (1) was fixed at a position separated by 50 mm from the edge of the bag member formed by the chassis. Further, the surface member and the waterproof sheet were directly joined with the aid of an adhesive agent applied to circles 10 mm in diameter on the portions of the waterproof sheet positioned correspondingly to the punched parts of the sheet (1). (These points of union are equivalent to six to seven point fixtures formed on a sheetlike article per 1,000 cm² of surface area). An absorbent article (12) was obtained by closing the cut in the waterproof sheet with an adhesive tape. The absorbent article (12) was evaluated by the following method. The results are shown in Table 7.

L: Method for evaluation of absorbent article (2)

A baby model provided with a ureter was prepared by imitating an infant weighing 10 kg. The absorbent article (12) produced in Example 36 was put on the baby model and artificial urine was discharged through the ureter at a speed of 50 ml/10 sec. into the absorbent article (12). The same urination was repeated after an interval of 50 minutes. The amount of the artificial urine absorbed by the absorbent article (12) until the artificial urine began to leak therefrom was used for evaluating the article's proofness against leakage of urine. The absorbent article which had succumbed to leakage of urine was removed from the baby model. The absorbent article was pressed in the center and the opposite sides thereof with a hand to evaluate the ease of migration of the absorbent resin which had swelled with absorbed urine.

Example 37

The procedure of Example 36 was repeated, except that a circle was punched at the center of a rectilinear line dividing the sheet (1) longitudinally into two equal halves and an adhesive agent was applied to the portion of the waterproof sheet corresponding to the punched portion. (The point of union thus formed was equivalent to two or three point fixtures per 1,000 cm² of surface area of a sheetlike article.) Thus, an absorbent article (13) was obtained. This absorbent article (13) was evaluated in the same manner as in Example 36. The results are shown in Table 7.

Example 38

The procedure of Example 36 was repeated, except that circles 15 mm in diameter were punched around two points dividing into three equal lengths a rectilinear line dividing the sheet (1) longitudinally into two equal halves and an adhesive agent was applied to the portions of the waterproof sheet corresponding to the punched portions. (The points of union thus formed herein were equivalent to four to five point fixtures formed on a sheetlike article per 1,000 cm² of surface area of the sheetlike article.) Thus, an absorbent article (14) was obtained. This absorbent article (14) was evaluated in the same manner as in Example 36. The results are shown in Table 7.

Control 17

An absorbent article (3c) for comparison was obtained by repeating the procedure of Example 36, except that the sheet (1) was incorporated in its unmodified form into the chassis of a disposable diaper. The absorbent article (3c) for comparison was evaluated in the same manner as in Example 36. The results are shown in Table 7.

TABLE 7

|  | Example 36 | Example 37 | Example 38 | Control 17 |
|---|---|---|---|---|
| Absorption Capacity of absorbent article (ml) | 350 | 300 | 350 | 300 |
| Migration of gel | ○ | Δ | ○ | × |

○: Nominal migration of gel
Δ: Small migration of gel
×: Large migration of gel

INDUSTRIAL APPLICABILITY

The absorbent material of this invention enjoys high safety due to exclusion of impurities, excels in suppleness and tough feeling, possesses an ideal ability to absorb liquid, and finds utility to various applications intended for absorption of water and moisture. The absorbent material of this invention is further capable of retaining high speed of absorption and high flexibility intact even when it is exposed to an atmosphere of low humidity for a long time. The absorbent material of this invention is incapable of shedding fine dust. It can be used for absorbent layers in sanitary materials, sheets intended to allow formation of dew and absorption of water, agricultural grade absorbent sheets, civil engineering grade water-cutoff agents, medical sheets, agents intended to keep perishable foodstuffs from deterioration, and absorbents intended to protect sundry goods, for example. By the method of production according with this invention, the absorbent material mentioned above can be procured very easily and inexpensively. Since the absorbent article of this invention is allowed to incorporate water-absorbent resin therein at a high concentration, it is thin and compact in spite of the fact that it possesses a capacity for absorption favorably comparable with that of the conventional article. Further, since this absorbent article has high flexibility, it ideally fits the contour of the user's body and enjoys high convenience of use. The absorbent article of this invention is thin and compact as compared with the conventional absorbent article and, nevertheless, possesses an excellent ability to absorb liquid. Even after this absorbent article has absorbed liquid, it does not suffer the absorbent resin wetted with the absorbed liquid to, migrate or deform. Moreover, it can be manufactured easily and economically. It, therefore, can be utilized in various applications which are aimed at absorbing water or moisture. As typical examples of the applications, absorbent layers in sanitary materials, sheets intended to allow formation of dew and absorption of water, agricultural grade absorbent sheets, civil engineering grade water-cutoff agents, medical sheets, agents intended to keep perishable foodstuffs from deterioration, and absorbents intended to protect sundry goods may be cited.

We claim:

1. An absorbent material comprising 100 parts by weight of absorbent resin particles and 15 to 150 parts by weight of water, said absorbent material being in the form of a sheet having a thickness in a range from about 0.3 to about 5 mm and formed by mutual adhesion of said absorbent resin particles.

2. An absorbent material according to claim 1, wherein the tensile yield strength is not less than 5 kg/cm$^2$ and the tensile yield elongation is not less than 20%.

3. An absorbent material according to claim 2, wherein said absorbent resin particles have a particle size distribution such that substantially none of said particles has a diameter of not less than 1,000 μm and not less than 20% by weight of said particles have diameters of not more than 150 μm.

4. An absorbent material according to claim 1, wherein the speed of absorption is not more than 50 seconds and the angle of rotation without cracking from a horizontal plane and about a straight line dividing the surface area of the absorbent material into two substantially equal parts is not less than 90 degrees.

5. An absorbent material according to claim 1, wherein said absorbent resin particles are capable of absorbing at least 20 ml of an aqueous 0.9 wt % sodium chloride solution per g thereof under a load of at least 20 g/cm$^2$.

6. An absorbent material according to claim 1, wherein said absorbent resin particles have undergone a surface cross-linking treatment.

7. An absorbent material according to claim 1, wherein said absorbent resin particles have a particle size distribution such that substantially none of said particles has a diameter of not less than 1,000 μm and not more than 10% by weight of said particles have diameters of not more than 150 μm.

8. An absorbent material according to claim 1, wherein said absorbent material, on contact with an aqueous liquid, is substantially disintegrated into individual absorbent resin particles.

9. A laminated absorbent material having a water-pervious sheet superposed on at least one surface of an absorbent material according to claim 1.

10. An absorbent article comprising an absorbent material according to claim 1 in a bag having at least one surface side thereof formed of a water-pervious sheet.

11. An absorbent material comprising 100 parts by weight of absorbent resin particles, 15 to 150 parts by weight of water, and 0.1 to 10 parts by weight of at least one absorption auxiliary selected from the group consisting of water-insoluble minute particles, surfactants, and fibers, said absorbent material being in the form of a sheet having a thickness in a range from about 0.3 to about 5 mm and formed by mutual adhesion of said absorbent resin particles.

12. An absorbent material according to claim 11, wherein the speed of absorption is not more than 30 seconds and the flexibility is not less than 90 degrees.

13. An absorbent material according to claim 11, wherein said absorbent resin particles are capable of absorbing at least 20 ml of an aqueous 0.9 wt % sodium chloride solution per g thereof under a load of at least 20 g/cm$^2$.

14. An absorbent material according to claim 11, wherein said absorbent resin particles have undergone a surface cross-linking treatment.

15. An absorbent material according to claim 11, wherein said absorbent resin particles have a particle size distribution such that substantially none of said particles has a diameter of not less than 1,000 μm and not more than 10% by weight of said particles have diameters of not more than 150 μm.

16. An absorbent material comprising 100 parts by weight of absorbent resin particles, 0.1 to 10 parts by weight of at least one absorption auxiliary selected from the group consisting of water-insoluble minute particles, surfactants, and fibers, 3 to 40 parts by weight of water, and 5 to 50 parts by weight of a polyhydric alcohol, said absorbent material being in the form of a sheet having a thickness in a range from about 0.3 to about 5 mm and formed by mutual adhesion of said absorbent resin particles.

17. An absorbent material according to claim 16, wherein the speed of absorption with aging is not more than 50 seconds and the flexibility with aging is not less than 90 degrees.

18. An absorbent material according to claim 16, wherein said absorbent resin particles are capable of absorbing at least 20 ml of an aqueous 0.9 wt % sodium chloride solution per g thereof under a load of at least 20 g/cm$^2$.

19. An absorbent material according to claim 16, wherein said absorbent resin particles have undergone a surface cross-linking treatment.

20. An absorbent material according to claim 16, wherein said absorbent resin particles have a particle size distribution such that substantially none of said particles has a diameter of not less than 1,000 μm and not less than 10% by weight of said particles have diameters of not more than 150 μm.

21. An absorbent material according to claim 16, wherein said polyhydric alcohol is at least one member selected from the group consisting of glycerol, polyglycerin, ethylene glycol, diethylene glycol, triethylene glycol, and trimethylene glycol.

22. An absorbent material according to claim 16, wherein the weight ratio of said polyhydric alcohol to said water is not less than 1.

23. An absorbent material according to claim 16, wherein said absorbent material, on contact with an aqueous liquid, is substantially disintegrated into individual absorbent resin particles.

24. A laminated absorbent material having a water-pervious sheet superposed on at least one surface of an absorbent material according to claim 16.

25. An absorbent article comprising an absorbent material according to claim 16 in a bag having at least one surface side thereof formed of a water-pervious sheet.

26. An absorbent article having an absorbent material contained in a bag having at least one surface side thereof formed of a water-pervious sheet, said absorbent material being a sheetlike material comprising at least 60% by weight of absorbent resin and is furnished with 3 to 15 point fixtures per about 1,000 $cm^2$ of surface area of said sheetlike material.

27. An absorbent article according to claim 26, wherein said absorbent material is an absorbent material comprising 100 parts by weight of absorbent resin particles and 15 to 150 parts by weight of water, which absorbent material is characterized by the fact that said absorbent material is in the form of a sheet having a thickness in the approximate range of about 0.3 to 5 mm and said form of a sheet results from mutual adhesion of said absorbent resin particles.

28. An absorbent article according to claim 26, wherein the numerical value (V/n) of the ratio of the inner volume (V ml) of said bag to the number (n) of said point fixtures is in the range of 100 to 1,000.

* * * * *